(12) United States Patent
Miller et al.

(10) Patent No.: US 7,605,367 B2
(45) Date of Patent: *Oct. 20, 2009

(54) EXPLOSIVES DETECTION USING DIFFERENTIAL MOBILITY SPECTROMETRY

(75) Inventors: Raanan A. Miller, Chestnut Hill, MA (US); Erkinjon G. Nazarov, Lexington, MA (US); David B. Wheeler, Haverhill, MA (US); Quan Shi, Westford, MA (US); John A. Wright, Billerica, MA (US); Gary A. Eiceman, Las Cruces, NM (US)

(73) Assignee: Sionex Corporation, Bedford, MA (US)

( * ) Notice: Subject to any disclaimer, the term of this patent is extended or adjusted under 35 U.S.C. 154(b) by 185 days.

This patent is subject to a terminal disclaimer.

(21) Appl. No.: 11/879,321

(22) Filed: Jul. 17, 2007

(65) Prior Publication Data

US 2008/0135745 A1 Jun. 12, 2008

Related U.S. Application Data

(63) Continuation of application No. 11/471,826, filed on Jun. 20, 2006, now Pat. No. 7,262,407, which is a continuation of application No. 10/821,812, filed on Apr. 8, 2004, now Pat. No. 7,129,482, and a continuation-in-part of application No. 10/462,206, filed on Jun. 13, 2003, now Pat. No. 7,005,632, and a continuation-in-part of application No. 10/321,822, filed on Dec. 16, 2002, now Pat. No. 6,806,463, which is a continuation-in-part of application No. 10/187,464, filed on Jun. 28, 2002, now Pat. No. 7,045,776, which is a continuation-in-part of application No. 09/358,312, filed on Jul. 21, 1999, now Pat. No. 6,495,823.

(60) Provisional application No. 60/530,518, filed on Dec. 18, 2003, provisional application No. 60/461,282, filed on Apr. 8, 2003.

(51) Int. Cl.
*B01D 59/44* (2006.01)
*H01J 49/40* (2006.01)

(52) U.S. Cl. .................. 250/288; 250/281; 250/282

(58) Field of Classification Search ......... 250/281–288, 250/290, 292–294
See application file for complete search history.

(56) References Cited

U.S. PATENT DOCUMENTS 2,615,135 A 10/1952 Glenn, Jr.

(Continued)

FOREIGN PATENT DOCUMENTS

SU 966583 10/1982

(Continued)

OTHER PUBLICATIONS

Beverly, M.B. et al., "A Rapid Approach for the Detection of Dipicolinic Acid in Bacterial Spores Using Pyrolysis/Mass Spectrometry," Rapid Communications in Mass Spectrometry, Vo. 10, 455-458 (1996).

(Continued)

*Primary Examiner*—Bernard E Souw
(74) *Attorney, Agent, or Firm*—Ropes & Gray LLP

(57) ABSTRACT

The invention relates generally to ion mobility based systems, methods and devices for analyzing samples and, more particularly, in some embodiments to compact GC-DMS systems, methods, and devices employing enhanced GC column temperature control and configurations to identify various sample constituents.

20 Claims, 25 Drawing Sheets

U.S. PATENT DOCUMENTS

| | | | |
|---|---|---|---|
| 2,818,507 | A | 12/1957 | Britten |
| 2,919,348 | A | 12/1959 | Bierman |
| 3,511,986 | A | 5/1970 | Llewellyn |
| 3,621,240 | A | 11/1971 | Cohen et al. |
| 3,931,589 | A | 1/1976 | Aisenberg et al. |
| 4,019,989 | A | 4/1977 | Hazewindus et al. |
| 4,025,818 | A | 5/1977 | Giguere et al. |
| 4,136,280 | A | 1/1979 | Hunt et al. |
| 4,201,921 | A | 5/1980 | McCorkle |
| 4,315,153 | A | 2/1982 | Vahrenkamp |
| 4,517,462 | A | 5/1985 | Boyer et al. |
| 4,761,545 | A | 8/1988 | Marshall et al. |
| 5,218,203 | A | 6/1993 | Eisele et al. |
| 5,298,745 | A | 3/1994 | Kernan et al. |
| 5,420,424 | A | 5/1995 | Carnahan et al. |
| 5,455,417 | A | 10/1995 | Sacristan |
| 5,479,815 | A | 1/1996 | White et al. |
| 5,508,204 | A | 4/1996 | Norman |
| 5,536,939 | A | 7/1996 | Freidhoff et al. |
| 5,654,544 | A | 8/1997 | Dresch |
| 5,723,861 | A | 3/1998 | Carnahan et al. |
| 5,736,739 | A | 4/1998 | Uber et al. |
| 5,763,876 | A | 6/1998 | Perinarides et al. |
| 5,789,745 | A | 8/1998 | Martin et al. |
| 5,801,379 | A | 9/1998 | Kouznetsov |
| 5,834,771 | A | 11/1998 | Yoon et al. |
| 5,838,003 | A | 11/1998 | Bertsch et al. |
| 5,869,344 | A | 2/1999 | Linforth et al. |
| 5,965,882 | A | 10/1999 | Megerle et al. |
| 6,066,848 | A | 5/2000 | Kassel et al. |
| 6,107,624 | A | 8/2000 | Doring et al. |
| 6,124,592 | A | 9/2000 | Spangler |
| 6,180,414 | B1 | 1/2001 | Katzman |
| 6,239,428 | B1 | 5/2001 | Kunz |
| 6,323,482 | B1 | 11/2001 | Clemmer et al. |
| 6,495,823 | B1 | 12/2002 | Miller et al. |
| 6,504,149 | B2 | 1/2003 | Guevremont et al. |
| 6,512,224 | B1 | 1/2003 | Miller et al. |
| 6,540,691 | B1 | 4/2003 | Philips |
| 6,621,077 | B1 | 9/2003 | Guevremont et al. |
| 6,639,212 | B1 | 10/2003 | Guevremont |
| 6,653,627 | B2 | 11/2003 | Guevremont |
| 6,690,004 | B2 | 2/2004 | Miller et al. |
| 6,703,609 | B2 | 3/2004 | Guevremont |
| 6,713,758 | B2 | 3/2004 | Guevremont |
| 6,753,522 | B2 | 6/2004 | Guevremont |
| 6,770,875 | B1 | 8/2004 | Guevremont |
| 6,774,360 | B2 | 8/2004 | Guevremont |
| 6,787,765 | B2 | 9/2004 | Guevremont |
| 6,799,355 | B2 | 10/2004 | Guevremont |
| 6,806,463 | B2 * | 10/2004 | Miller et al. ........ 250/286 |
| 6,806,466 | B2 | 10/2004 | Guevremont |
| 7,005,632 | B2 * | 2/2006 | Miller et al. ........ 250/287 |
| 7,129,482 | B2 * | 10/2006 | Miller et al. ........ 250/288 |
| 7,262,407 | B2 * | 8/2007 | Miller et al. ........ 250/286 |
| 2001/0030285 | A1 | 10/2001 | Miller et al. |
| 2002/0070338 | A1 | 6/2002 | Loboda |
| 2002/0134932 | A1 | 9/2002 | Guevremont et al. |
| 2003/0020012 | A1 | 1/2003 | Guevremont et al. |
| 2003/0038235 | A1 | 2/2003 | Guevremont et al. |
| 2003/0052263 | A1 | 3/2003 | Kaufman et al. |
| 2003/0089847 | A1 | 5/2003 | Guevremont et al. |
| 2003/0132380 | A1 | 7/2003 | Miller et al. |
| 2004/0094704 | A1 | 5/2004 | Miller et al. |
| 2006/0289745 | A1 * | 12/2006 | Miller et al. ........ 250/294 |
| 2007/0272852 | A1 * | 11/2007 | Miller et al. ........ 250/288 |
| 2008/0128612 | A1 * | 6/2008 | Miller et al. ........ 250/286 |
| 2008/0135745 | A1 * | 6/2008 | Miller et al. ........ 250/282 |
| 2008/0149824 | A1 * | 6/2008 | Miller et al. ........ 250/287 |

FOREIGN PATENT DOCUMENTS

| | | |
|---|---|---|
| SU | 1337934 | 9/1987 |
| SU | 1627984 | 7/1988 |
| SU | 1412447 | 6/1998 |
| SU | 1405489 | 10/1998 |
| SU | 1485808 | 10/1998 |
| WO | WO 97/38302 | 10/1997 |
| WO | WO 00/08454 | 2/2000 |
| WO | WO 00/08455 | 2/2000 |
| WO | WO 00/08456 | 2/2000 |
| WO | WO 00/08457 | 2/2000 |
| WO | WO 01/08197 | 2/2001 |
| WO | WO 01/22049 A2 | 3/2001 |
| WO | WO 01/35441 | 5/2001 |
| WO | WO-01/69217 | 9/2001 |
| WO | WO 01/69220 | 9/2001 |
| WO | WO 01/69647 | 9/2001 |
| WO | WO 02/071053 | 9/2002 |
| WO | WO 02/083276 | 10/2002 |
| WO | WO 03/005016 | 1/2003 |
| WO | WO 03/015120 | 2/2003 |

OTHER PUBLICATIONS

Dworzanski, J.P. et al., "Field-Portable, Automated Pyrolysis-GC/IMS System for Rapid Biomarker Detection in Aerosols: A Feasibility Study," Field Analytical Chemistry and Technology, vol. 1, No. 5, 295-305, (1997).

Krylov, E.V., "Comparison of the Planar and Coaxial Field Asymmetrical Waveform Ion Mobility Spectrometer (FAIMS)," International Journal of Mass Spectrometry, 225, (2003) pp. 39-51.

Krylova, N. et al., "Effect of Moisture on the Field Dependence of Mobility for Gas-Phase Ions of Organophosphorus compounds at Atmospheric Pressure with Field Asymmetric ion Mobility Spectrometry," J. Phys. Chem. A, vol. 107, 3648-3654.

Snyder, A.P., "Detection of the Picolinic Acid Biomarker in Bacillus Spores Using a Potentially Field-Portable Pyrolysis—Gas Chromatography—Ion Mobility Spectrometry System," Field Analytical Chemistry and Technology, vol. 1, No. 1, pp. 49-58 (1996).

Thornton, S.N. et al., "Feasibility of Detecting Dipicolinic Acid in Bacillus Spores Using a Handheld IMS Device with Pyrolysis GC," Proceedings of the 1994 ERDEC Scientific Conference on Chemical and Biological Defense Research, Nov. 1994, Aberdeen Proving Grounds, MD, 1996, pp. 601-607.

Thornton, S.N. et al., "Pyrolysis-Gas Chromatography/Ion Mobility Spectrometry Detection of the Dipicolinic Acid Biomarker in Bacillus Subtilis Spores During Field Bioaerosol Releases," Field analytical Methods for Hazardous Wastes and Toxic Chemicals: Proceedings of a Specialty Conference, Jan. 1997, Las Vegas, NV.

"A Micromachined Field Driven Radio Frequency-Ion Mobility Spectrometer for Trace Level Chemical Detection," A Draper Laboratory Proposal Against the "Advanced Cross-Enterprise Technology Development for NASA Missions," Solicitation, NASA NRA 99-OSS-05.

Barnett, D.A. et al., "Isotope Separation Using High-Field Asymmetric Waveform Ion Mobility Spectrometry," Nuclear Instruments & Methods in Physics Research (2000), pp. 179-185, 450(1).

Basile, F., "A Gas Sample Pre-concentration Device Based on Solid Phase Microextraction (SPME) and Temperature Programmed Desorption (TPD)," Instrumentation Sci. Tech., (2003), pp. 155-164, 31(2).

Buryakov, I.A. et al., "A New Method of Separation of Multi-Atomic Ions by Mobility at Atmospheric Pressure Using a High-Frequency Amplitude-Asymmetric Strong Electric Field," International Journal of Mass Spectrometry and Ion Processes (1993), pp. 143-148, 128.

Buryakov, I.A. et al., "Drift Spectrometer for the Control of Amine Traces in the Atmosphere," J. Analytical Chem., (1993), pp. 156-165, 48(1).

Buryakov, I.A. et al., "Separation Ions According to Mobility in a Strong ac electric Field," Sov. Tech. Phs. Lett. (1991), pp. 446-447, 17(6).

Buryakov, I.A. et al., Device and Method For Gas Electrophoresis, Chemical Analysis fo Environment, edit. Prof. V.V. Malakhov, Novosibirsk; Nauka (1991), pp. 113-127.

Carnahan, B. et al., "Field Ion Spectrometry—A New Analytical Technology for Trace Gas Analysis," ISA, (1996), pp. 87-96, 51(1).

Carnahan, B. et al., "Field Ion Spectrometry—A New Technology for Cocaine and Heroin Detection," SPIE, (1997), pp. 106-119, 2937.

Guevremont, R. and Purves, R., "High Field Asymmetric Waveform Ion Mobility Spectometry-Mass Spectrometry: An Investigation of Leucine Enkephalin Ions Produced by Electrospray Ionization," J. Am. Soc. Mass. Spectrom, (1999), pp. 492-501, 10.

Guevremont, R. et al., "Calculation of Ion Mobilities From Electrospray Ionization High Field Asymmetric Waveform Ion Mobility Spectrometry Mass Spectrometry," Journal of Chemical Physics, (2001), pp. 10270-10277, 114(23).

Geuvremont, R. et al., "Atmospheric Pressure In Focusing in a High-Field Asymmetric Waveform Ion Mobility Spectrometer," Review of Scientific Instruments, (1999), pp. 1370-1383, 70(2).

Handy, R. et al., "Determination of nanomlar levels of perchlorate in water by ESI-FAIMS-MS," JAAS (2000), pp. 907-911, 15.

Krylov, E.V., "A Method of Reducing Diffusion Losses in a Drift Spectrometer," Technical Physics, (1999), pp. 113-116, 4d(1).

Krylov, E.V., "Pulses of Special Shapes Formed on a Capacitive Load," Instruments and Experimental Techniques, (1997), pp. 628, 40(5).

Miller, R.A. et al., "A MEMS Radio-Frequency Ion Mobility Spectrometer for Chemical Agent Detection," (Jun. 2000) Proceedings of the 2000 Solid State Sensors and Actuators Workshop, Hilton Head, SC.

Miller, R.A. et al., "A Novel Micromachined High-Field Asymmetric Waveform-Ion Mobility Spectrometer," Sensors and Actuators B, (2000) pp. 300-306, B67 (3).

Phillips, M., "Method for the Collection and Assay of Volatile Organic Compounds in Breath," Analytical Biochemistry, (1997), pp. 272-278, 247.

Pilzecker, P. et al., "On-Site Investigations of Gas Insulated Substations Using Ion Mobility Spectrometry for Remote Sensing of SF6 Decomposition," IEEE, (2000), pp. 400-403.

Riegner, D.E. et al., "Qualitative Evaluation of Field Ion Spectrometry for Chemical Warfare Agent Detection," Proceedings of the ASMS Conference on Mass Spectrometry and Allied Topics (Jun. 1997), pp. 473A-473B.

Schneider, A. et al., "High Sensitivity GC-FIS for Simultaneous Detection of Chemical Warfare Agents," Mine Safety Appliances Co., Pittsburgh, PA, USA, (2000), AT-Process, pp. 124-136, 5(3,4), CODEN: APJCFR ISSN: 1077-419X.

Shute, L.A. et al., "Curie-point Pyrolysis Mass Spectrometry Applied to Characterization and Identification of Selected Bacillus Species," J. General Micro., (JGMIAN) (1984), pp. 343-355, 130(2).

Eiceman, et al., "Miniature radio-frequency mobility analyzer as a gas chromatographic detector for oxygen-containing volatile organic compounds, pheromones and other insect attractants," J. Chrom., pp. 205-217, 917 (2001).

* cited by examiner

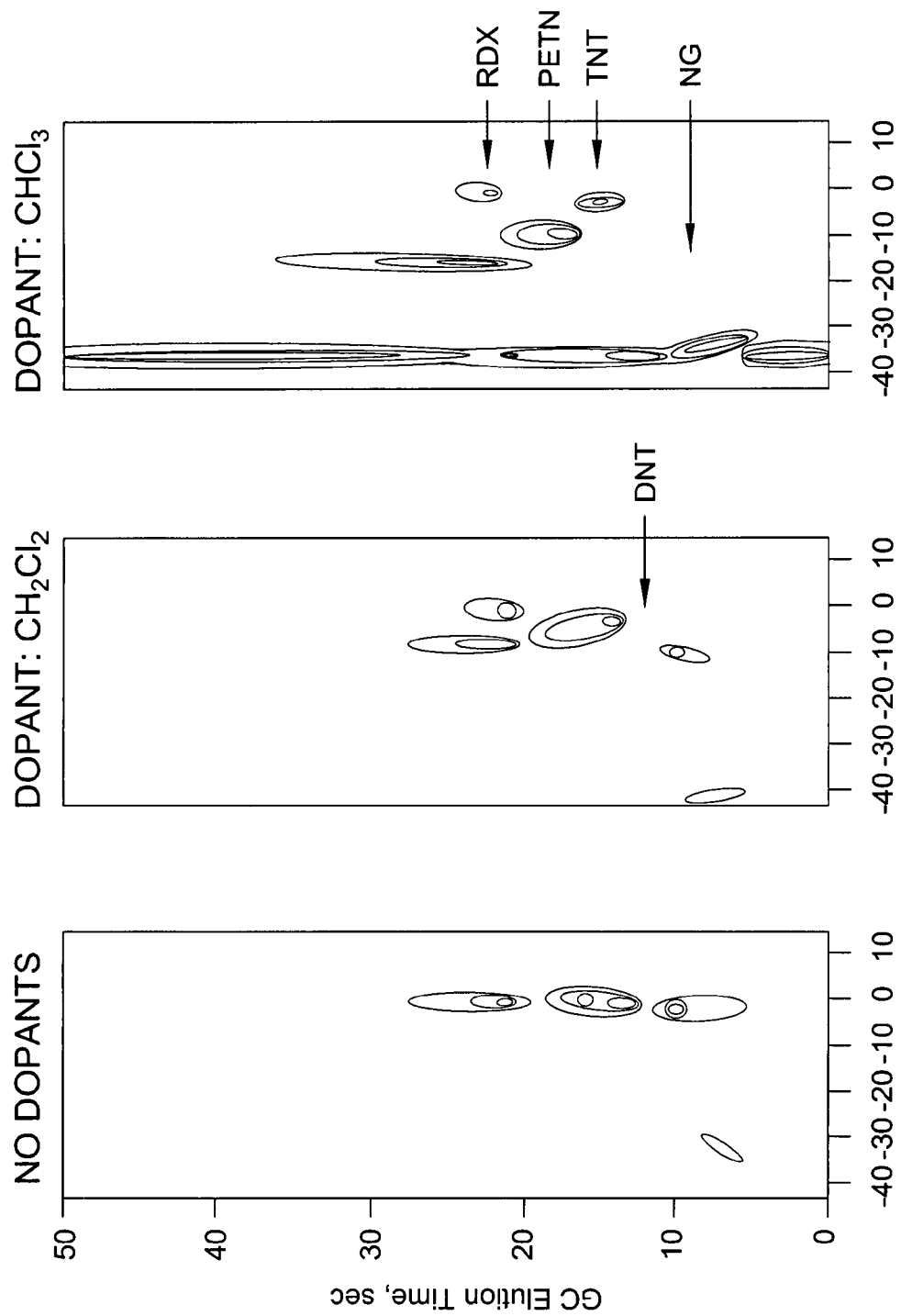

| Explosive/Taggant | No Dopant | CH2Br2, 2% | CH2Cl2, 2.5% | CH3OH, 1% | Isopropanol, 2% |
|---|---|---|---|---|---|
| HMX t=95 sec | V, Negative Vc=-0.23 Rf 950V, Air, 120 C, 1atm long drag, inlet T 150->190C, Oven T 50->100C, 80C/m->100C/m | V, Negative Vc=-4.9 Rf 950V, Air, 120 C, 1atm long drag, inlet T 150->190C, Oven T 50->100C, 80C/m->100C/m | V, Negative Vc=-6.1 Rf 950V, Air, 120 C, 1atm long drag, inlet T 150->190C, Oven T 50->100C, 80C/m->100C/m | GC temperature was low, HMX did not move. | Not measured |
| Tetryl t=116 sec t=160 sec | V, Negative Vc=-0.23 Rf 950V, Air, 120 C, 1atm inlet T 150, Oven T 50, 80C/min split 5:1, f=8 cc/min unless specifically noted, other molecules are under same GC conditions | Not measured | Two peaks Vc=-1.99, -6.68, Rf 950V, Air, 120 C, 1atm | V, Negative Vc=-0.82 Rf 950V, Air, 120 C, 1atm | Not measured |
| PETN t=104 sec | V, Negative Vc=-0.23 Rf 950V, Air, 120 C, 1atm mix6x10 | V, Negative Vc=-7.9 Rf 1050V, N2, 120 C, 1atm, 1 uL, 0.1 mg/ml long drag | V, Negative Vc=-5.51 Rf 950V, Air, 120 C, 1atm, mix6x10 | V, Negative Vc=-1.5 Rf 950V, Air, 120 C, 1atm, mix6x10 GC column flow was low | V, Negative Vc=-5.51 Rf 1050V, N2, 120 C, 1atm, 1 uL, 0.1 mg/ml |

Fig. 9 (part 1)

| Explosive/ Taggant | No Dopant | CH2Br2, 2% | CH2Cl2, 2.5% | CH3OH, 1% | Isopropanol, 2% |
|---|---|---|---|---|---|
| RDX<br>t=37 sec(+)<br>t=72 sec(-) | V, Negative<br>V, Positive<br>Vc=-0.3, --negative<br>Vc=-4.92, --positive<br>Rf 950V, Air, 120 C, 1atm, mix6x10<br>Pos and neg are at different retention time, break down effect | V, Negative<br>Vc=-9,<br>Rf 1050V, N2, 120 C, 1atm, 1 uL, 0.1 mg/ml | V, Negative<br>V, Positive<br>Vc=-8.43, --negative<br>Vc=-6.68, --positive<br>Rf 950V, Air, 120 C, 1atm, mix6x10<br>Pos and neg are at different retention time, break down effect | V, Negative<br>Vc=-2.58,<br>Rf 950V, Air, 120 C, 1atm, mix6x10<br>no Pos ion shown, MeOH depressed it. | V, Negative<br>Vc=-6.68,<br>Rf 1050V, N2, 120 C, 1atm, 1 uL, 0.1 mg/ml |
| NG<br>t=31 sec | V, Negative<br>Two Peaks<br>Vc=-0.23, -20.7,<br>Rf 950V, Air, 120 C, 1atm, mix6x10 | V, Negative<br>Vc=-10,<br>Rf 1050V, N2, 120 C, 1atm, 1 uL, 0.1 mg/ml | V, Negative<br>one peak<br>Vc=-9.6,<br>Rf 950V, Air, 120 C, 1atm, mix6x10 | V, Negative<br>Two peaks<br>Vc=-2.58, -33.7,<br>Rf 950V, Air, 120 C, 1atm, mix6x10 | V, Negative<br>Vc=-10,<br>Rf 1050V, N2, 120 C, 1atm, 1 uL, 0.1 mg/ml |
| TNT<br>t=72 sec | V, Negative<br>Vc=-0.82,<br>Rf 950V, Air, 120 C, 1atm, mix6x10 | X | V, Negative<br>Vc=-2.58,<br>Rf 950V, Air, 120 C, 1atm, 2 uL, 0.1 mg/ml<br>peak too close to MeCl2 (-36 V) | V, Negative<br>Vc=-0.82,<br>Rf 950V, Air, 120 C, 1atm, mix6x10 | V, Negative<br>Vc=-10,<br>Rf 1050V, N2, 120 C, 1atm, 1 uL, 0.1 mg/ml |
| EGDN<br>t=10 sec | V, Negative<br>Vc=-20,<br>Rf 950V, Air, 120 C, 1atm, mix6x10 | X | V, Negative<br>Vc=-34,<br>Rf 950V, Air, 120 C, 1atm, mix6x10 | V, Negative<br>Vc=-33.7,<br>Rf 950V, Air, 120 C, 1atm, mix6x10 | V, Negative<br>Vc=-30,<br>Rf 850V, Air, 120 C, 1atm, 1 uL, 0.1 mg/ml<br>peak too close to Isopropanol (-32 V) |
| DNT<br>t=48 sec | V, Negative<br>Vc=-1.7<br>Rf 950V, Air, 120 C, 1atm, mix6x10 | no peaks | X<br>no peaks | V, Negative<br>Vc=-2<br>Rf 950V, Air, 120 C, 1atm, mix6x10 | V, Negative<br>Vc=-16.7<br>Rf 950V, N2, 120 C, 1atm, weak signal decreased by 20 times |

Fig. 9 (part 2)

| Explosive/Taggant | No Dopant | CH2Br2, 2% | CH2Cl2, 2.5% | CH3OH, 1% | Isopropanol, 2% |
|---|---|---|---|---|---|
| ... | ... | ... | ... | ... | ... |
| o-MNT Taggant t=16 sec | V, Positive<br>Vc=-17.8, Rf 950V, Air, 120 C, 1atm, too close to RIP | Not measured | V, Positive<br>Vc=-14.3, Rf 950V, Air, 120 C, 1atm, too close to RIP | X | Not measured |
| p-MNT Taggant 19 sec | V, Positive<br>Vc=-16.7, Rf 950V, Air, 120 C, 1atm, too close to RIP | | V, Positive<br>Vc=-14.9, Rf 950V, Air, 120 C, 1atm, too close to RIP | X | Not measured |
| DMNB t=17 sec | V, Positive<br>Vc=-7.9, Rf 950V, Air, 120 C, 1atm | Not measured | V, Positive<br>Vc=-9, Rf 950V, Air, 120 C, 1atm | X | |
| TATP t=13 sec | V, Positive<br>Vc=-8.43, Rf 950V, Air, 120 C, 1atm | | V, Positive<br>Vc=-10.8, Rf 950V, Air, 120 C, 1atm | V, Positive<br>Vc=-5, Rf 950V, Air, 120 C, 1atm | X |
| HMTD t=49 sec | V, Positive<br>Vc=1.5, Rf 950V, Air, 120 C, 0.6atm old sample | Not measured | V, Positive<br>Vc=-1.4, Rf 950V, Air, 120 C, 1atm new sample | V, Positive<br>Vc=-0.82, Rf 950V, Air, 120 C, 1atm old sample | X |
| | V, Negative<br>V, Positive | Not measured | V, Negative<br>V, Positive | Not measured | V, Negative |
| AN t(+)=3 sec t(-)=6 sec | Vc=-19.6,--negative<br>Vc=-19.6,--positive<br>Rf 950V, air, 120 C, 1atm<br>Pos and neg are at different retention time, break down to NH3 (+) and HNO3(-) | | Vc=-41.83, --negative<br>Vc=-24.3, --positive<br>Rf 950V, air, 120 C, 1atm<br>Pos and neg are at different retention time, break down to NH3 (+) and HNO3(-) | | Vc=-3.75, Rf 950V, Air, 120 C, 1atm, mix6x10 no Pos ion shown, Isopropanol depressed it. |

Fig. 9 (part 3)

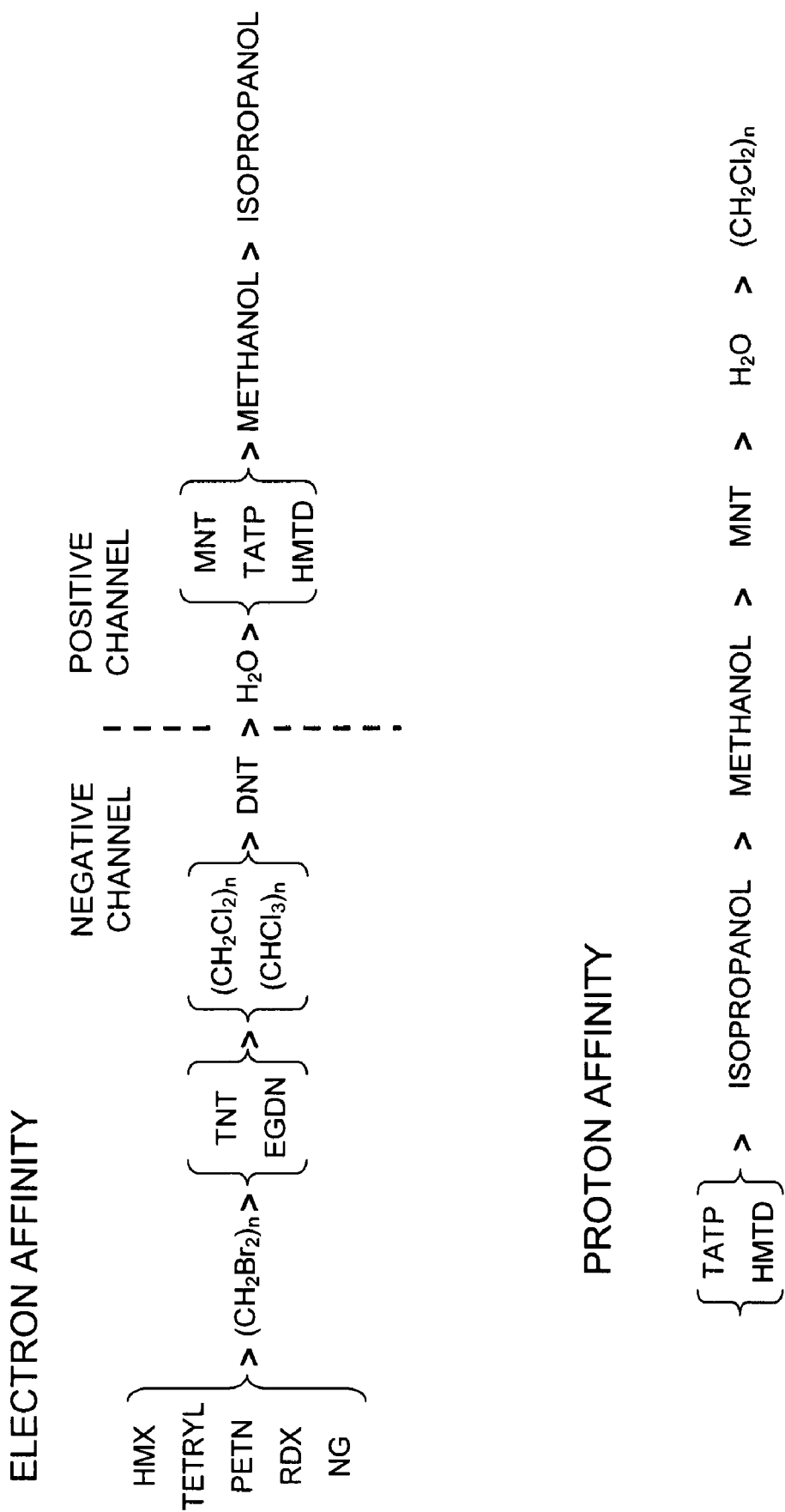

EXPLOSIVES DETECTION USING DIFFERENTIAL MOBILITY SPECTROMETRY

REFERENCE TO RELATED APPLICATIONS

This application is a continuation of U.S. patent application Ser. No. 11/471,826, filed on Jun. 20, 2006, which is a continuation of U.S. patent application Ser. No. 10/821,812, filed on Apr. 8, 2004, which is a continuation-in-part of U.S. patent application Ser. No. 10/187,464, filed Jun. 28, 2002, and a continuation-in-part of U.S. patent application Ser. No. 10/462,206, filed Jun. 13, 2003, and also a continuation-in-part of U.S. patent application Ser. No. 10/321,822, filed Dec. 16, 2002, which is a continuation-in-part of U.S. patent application Ser. No. 09/358,312, filed Jul. 21, 1999, now U.S. Pat. No. 6,495,823 B1. The U.S. patent application Ser. No. 10/821,812 also claims the benefit of U.S. Provisional application No. 60/461,282, filed Apr. 8, 2003 and U.S. Provisional application No. 60/530,518, filed Dec. 18, 2003, the entire contents thereof are incorporated herein by reference in their entirety.

FIELD OF THE INVENTION

The present invention relates generally to identification of unknown constituents of a sample by their ion mobility characteristics in an electric field, and more particularly to devices and methods that analyze compounds via high field asymmetric waveform ion mobility spectrometry.

BACKGROUND

There are many situations where it is desired to identify chemical compounds in a sample. Such samples may be taken directly from the environment or they may be provided by front end specialized devices to separate or prepare compounds before analysis. Furthermore, recent events have seen members of the general public exposed to dangerous chemicals in situations where previously no thought was given to such exposure. There exists, therefore, a demand for low cost, accurate, easy to deploy and use, reliable devices capable of identifying the chemical content of a sample.

As well, recent events have brought renewed interest to the addition of taggants to explosive materials for security purposes. Use of taggants serves two different functions and thus uses two different kinds of taggants. Detection taggants are materials added to explosives that can be sensed prior to detonation by appropriate detection equipment. Identification taggants are additives designed to survive an explosive blast, to be recoverable at the bomb scene, and to provide traceable sourcing information related to the explosives' purchase history.

Taggant options include addition of volatile chemicals, radioisotopes and the like. In countries participating under international commercial air security conventions, one of several volatile chemicals can be used to mark plastic explosives for detection. The United States has officially designated 2,3-dimethyl-2,3-dinitro-n-butane ($C_6H_{12}N_2O_4$), commonly referred to as DMNB, as a detection taggant for plastic explosives.

These taggants and other explosive compounds can be detected with various analytical equipment. One class of known chemical analysis instruments is referred to as mass spectrometers. Mass spectrometers are generally recognized as being one of the most accurate type of detectors for compound identification, given that they can generate a fingerprint pattern for even fragment ions. However, mass spectrometers are quite expensive and large and are relatively difficult to deploy in the field. Mass spectrometers also suffer from other shortcomings such as the need to operate at low pressures, resulting in complex support systems. These systems also require a highly trained user to tend to operations and interpret results.

Another class of known chemical analysis instruments enable use of atmospheric-pressure chemical ionization. Ion analysis is based on the recognition that ion species have different ion mobility characteristics under different electric field conditions at elevated pressure conditions including atmospheric pressure. Practices of the concept include time-of-flight Ion Mobility Spectrometry (IMS) and differential mobility spectrometry (DMS), the latter also sometimes referred to as field asymmetric waveform ion mobility spectrometry (FAIMS). These systems enable chemical species identification at atmospheric pressure, preferably based on dry and clean gas samples.

In a conventional time-of-flight IMS device (sometimes referred to as TOF-IMS), a propelling DC field gradient and a counter gas flow are set and an ionized sample is released into the field which flows to a collector electrode. Ion species are identified based on the DC field strength and time of flight of the ions to the collector. The ion mobility is constant when the electric field is weak.

DMS systems identify ion species by mobility behavior in a compensated high asymmetric RF field, where ions flow in a carrier gas and are shifted in their path by a high-low varying electric field. The conventional DMS operates with a selected Vrf and species detections are correlated with a preset, or scanned, DC compensation voltage ($V_c$) applied to the RF field. Species are identified based upon correlation of Vrf and $V_c$ with historical detected data. The amount of compensation depends upon species characteristics and the selected compensated field conditions.

A typical DMS device includes a pair of opposed filter electrodes defining an analytical gap between them in a flow path (also known as a drift tube). Ions flow into the analytical gap. The asymmetric RF field (sometimes referred to as a filter field, a dispersion field or a separation field) is generated between the electrodes transverse to the carrier gas/ion flow in the gap. Field strength, E, varies as the applied RF voltage, Vrf (sometimes referred to as dispersion or separation voltage) and size of the gap between the electrodes. Such systems can operate at atmospheric pressure.

Ions are displaced transversely by the RF field, with a given species being displaced a characteristic amount toward the electrodes per cycle. The DC compensation voltage ($V_c$) is applied to the electrodes along with the Vrf to compensate the displacement of a particular species. Now the applied compensation will offset transverse displacement generated by the applied Vrf for that particular ion species. The result is zero or near-zero net transverse displacement of that species, which enables that ion species to pass through the filter for detection. All other ions undergo a net displacement toward the filter electrodes and will eventually be neutralized upon contact with one of the filter electrodes.

If the compensation voltage is scanned for a given RF field, a complete spectrum of ion species in the sample can be produced. The recorded image of this spectral scan is sometimes referred to as a "mobility scan", as an "ionogram", or as "DMS spectra". The time required to complete a scan is system dependent.

DMS operates based on the fact that an ion species will have an identifying property of high and low field mobility in the analytical RF field. Thus DMS detects differences in an ion's mobility between high and low field conditions and classifies the ions according to these differences. These differences reflect ion properties such as charge, size, and mass as well as the collision frequency and energy obtained by ions between collisions and therefore enables identification of ions by species.

Various chemical species in a sample can be identified according to the conventional DMS process. However, accurate identification of several species in a sample whose detection spectra overlap is difficult. This is in part due to the fact that DMS detection peaks are relatively broad compared to a mass spectrometer, so overlap is more likely than with a mass spectrometer. In fact, where several ion species exhibit similar behavior in the DMS filter field their associated DC compensation will be very close, and so their detection spectra (detection peaks) may overlap.

This "overlap" of detection peaks can interfere with species identification. But discrimination between overlapping spectra is not easily achieved and similar species may be difficult to separate from each other.

Furthermore, false negative detections are perilous when dangerous compounds, such as explosives, are at issue, whereas false positives can reduce trust in a detection system. Therefore improved spectrometer performance is an important goal.

It would therefore be desirable to provide a system and method for detecting ions with a differential ion mobility spectrometer (DMS, also known as a Field Asymmetric waveform Ion Mobility Spectrometer (FAIMS)), with enhanced sensitivity and discrimination between ion species. It would also be desirable to find optimal selectivity conditions by modifying transport gas modifiers and concentrations, in particular for detecting explosives by using a compact "micro-fabricated" DMS device.

Furthermore, while prior art IMS system scans take on the order of a second to complete, prior art DMS scans may take on the order of 10 seconds to complete. It would therefore be desirable to provide a DMS-based explosives detection system that enables rapid characterization of a chemical sample and accurate identification of explosives and capable of performing DMS scans in only a second or even a fraction of a second.

SUMMARY

The invention is directed to systems and methods for detection and identification of explosives-related compounds, (e.g., explosives or indicators of explosives like taggants) in a chemical sample by differential ion mobility spectrometry (DMS). The invention provides an explosives detector based on aspects of differential ion mobility and with enhanced separation of ion species of interest. Embodiments achieve improved resolution between detection peaks and increased detection sensitivity. Preferred embodiments are fast operating, both with or without a pre-separator front-end.

In embodiments of the invention, we can detect taggants, such as DNMB, in order to detect presence of an explosive. We can also detect explosive materials per se in practice of the invention, and we can achieve improved species discrimination by use of a dopant in the DMS system, We can also selectively improve peak separation (resolution) by control of pressure in the internal DMS operating environment. Furthermore, we can achieve rapid and reliable explosives detection by use of a compactly packaged and fast-operating "plate-type" DMS system of the invention.

A system of the present invention includes a DMS ion filter in a filter section located in a flow path after a sample delivery section. The sample delivery section is for receipt of sample and delivery of ionized sample flow to the filter section. The filtered/separated ion species of interest pass through the ion filter section and flow to an output section of the flow path. Preferably the output section has a detector, wherein detection of ion species passed by the ion filter is correlated with the analytical device conditions, and this data is compared to a lookup table or other device. Upon a data match to known data, a species detection can be identified and presence of an associated analyte of interest in the sample (e.g., detection of an indicator of presence of an explosive compound) can be indicated.

Preferably the output section includes a two channel, or two mode, detector, i.e., it is capable of detection positive and negative modes (ion species) simultaneously. These modes can be related back to the ionized and filtered sample to assist in ion species and analyte identification. More specifically, a compound may be represented by either or both positive and negative ions, as such modes may be generated by ionization of the analyte molecules. In a preferred embodiment, both positive and negative modes of an ionized species can be simultaneously detected in a detection and identification section of the output. In this case, the detector includes biased detector electrodes that are capable of simultaneous detection of modes simultaneously passed by the DMS filter.

Quite favorably, configuration of the flow path of a preferred embodiment of the invention enables both modes of an ionized sample to flow into the DMS filter. The DMS filter can pass both positive and negative modes and which can be detected simultaneously within the time frame of a mobility scan, wherein each species mode is passed when the scanned field conditions are appropriate for that species not to be neutralized. Thus an analyte may produce ions positive and negative species and each will pass through the filter at the appropriate signature field conditions. This scanned data enable a more complete detection data and more reliable identification than having only one mode as might be detected from systems only capable of single mode detection (by structural constraints, by slow cycle times, or the like.

Preferred embodiment of the invention are compact and fast operating with fast scan rates and in addition benefit from dual mode capability. The result is fast and more reliable explosives detection in a compact and even portable system.

In accordance with the present invention, discrimination of ions from each other according to mobility differences is achieved wherein the RF field and the selected compensation enables a particular ion species to pass though the filter. A plot of detection intensity versus compensation for a given FR field strength identifies an in species by its characteristic mobility differences in the compensated high-low varying DMS field. Species can be identified according to the applied conditions and peak location along the Vc axis. Peak height indicates detection intensity for those conditions and which may be correlated with detection quantity.

Furthermore, in a GC-DMS apparatus of the invention, pre-separation of the sample using a GC refines the sample and eases the competitive ionization that occurs with an unseparated sample. This is useful but not essential and practices of the invention detect explosive-related materials by direct sampling. However, use of a GC also adds retention time as an additional indicator of detected species. As a result DMS data and retention time can be correlated to provide orthogonal detection data for still more reliable explosives identifications.

Furthermore, a preferred "plate-type" DMS is disclosed which can perform DMS scans in a second or less and even in milliseconds, while prior art DMS devices can take many seconds to perform a single scan.

In a preferred embodiment single mode or dual mode detection data is combined with filter field parameter data and this is combined with the separation data representing a first pre-separation (SPE, SPME, GC or the like) to enable highly reliable identification of the analyte of interest, even at trace levels.

The foregoing description supports a multitude of embodiments. For example, a compact and reliable smart explosives detection system can be deployed in buildings or as portable devices. Meanwhile, some embodiments of the present invention may be practiced in method and apparatus using the above preferred DMS or may use coaxial cylindrical, planar, radial and other DMS electrode configurations and still will remain within the spirit and scope of the present invention.

Further features and advantages of the present invention will be apparent from the following description of preferred embodiments and from the claims.

BRIEF DESCRIPTION OF THE DRAWINGS

The following figures depict certain illustrative embodiments of the invention in which like reference numerals refer to like elements. These depicted embodiments are to be understood as illustrative of the invention and not as limiting in any way.

FIGS. 6A-6C show DMS spectra for a mixture of explosives without dopant (A), with $CH_2Cl_2$ as dopant (B), and with $CHCl_3$ as dopant (C) in practice of an embodiment of the invention;

FIG. 9 shows Table 2 with a listing of illustrative experimental conditions and results obtained for a combination of several explosives/taggants and dopants in practice of an embodiment of the invention;

FIG. 10 is a diagram of the relative electron affinities and proton affinities for exemplary explosives and dopants in practice of an embodiment of the invention

ILLUSTRATIVE DESCRIPTION

In general, the invention is directed to systems and methods for detecting and identifying unknown constituents in chemical substances by aspects of differential ion mobility. In particular, the systems and methods described herein can be used to detect explosives-related compounds, whether explosives material per se or taggants or the like used with explosives, using DMS technology.

Figure 1A:
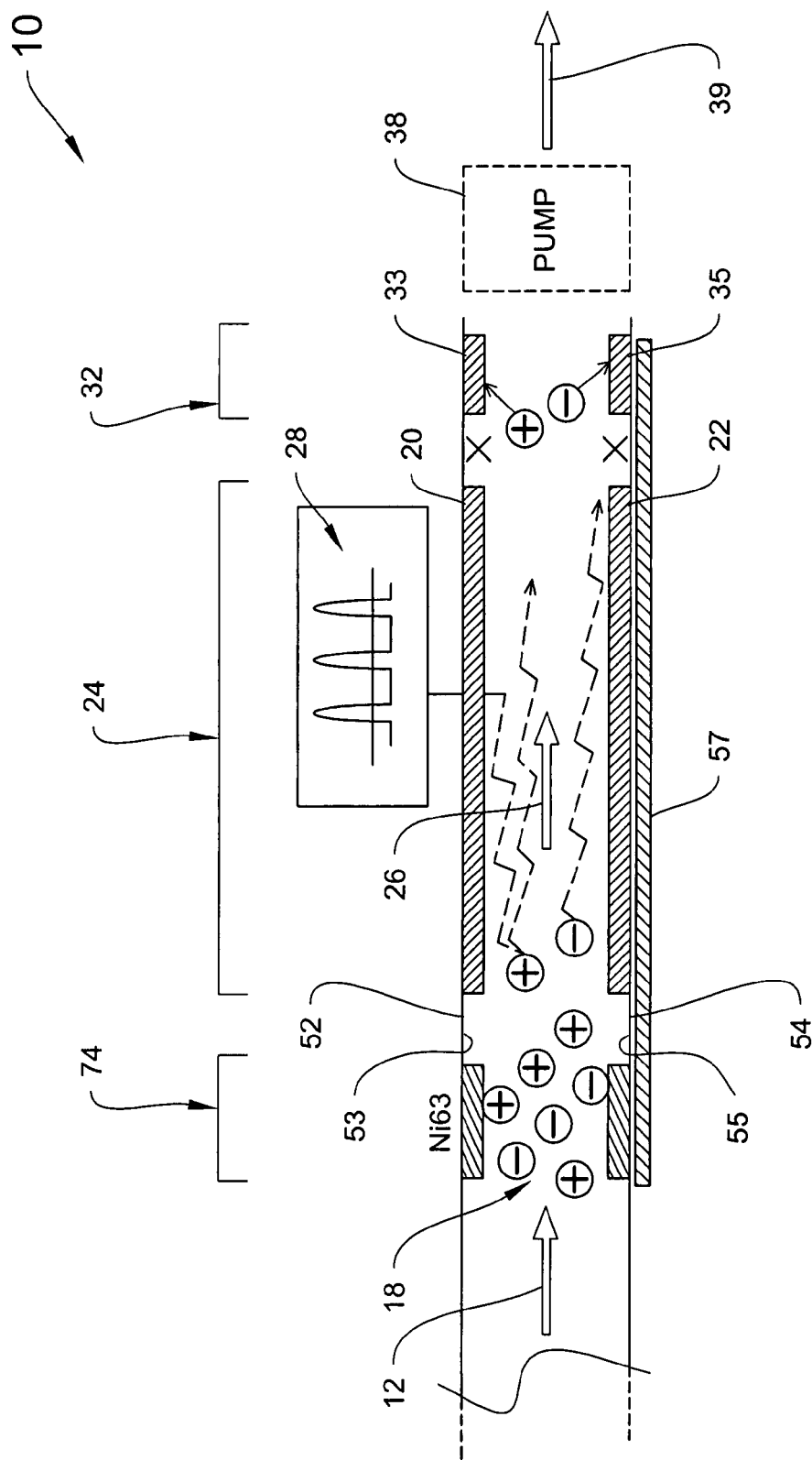
FIGS. 1A-1E show a schematic diagram of a Differential Ion mobility Spectrometer (DMS) in practice of an embodiment of the invention.

An illustrative DMS system of the invention is shown in FIG. 1A, which is a schematic block diagram of a DMS spectrometer 10, which operates by drawing a fluid (e.g., gas), indicated by arrow 12, via an optional pump 38 into an ionization region 18. The sample flow, e.g., a gas flow carrying an analyte(s) to be detected, is subjected to an ionization source, wherein at least the analyte is ionized although the carrier gas is normally part of the ionization process as well, for example by a radioactive $^{63}Ni$ source, UV lamp, plasma source, or the like.

The ionized sample passes between electrode plates 20 and 22 of ion filter 24, which may be assisted by use of a transport mechanism, such as a transport gas flow. An asymmetric high-low oscillating RF electric field driven by an RF voltage generator 28 is developed between the electrodes transverse to the gas flow between the ion filter plates 20 and 22. The ions move in the asymmetric field with a zigzag motion along the flow path 26. Without an additional applied bias voltage, only ions whose displacement during high field cycle equals their displacement during the low field cycle pass through the ion filter. All other ions will be driven into the filter electrodes and are neutralized by contact. Once neutralized, the neutral molecules will be transported by the transport gas out of the filter. The passed ion species is detected downstream, such as at detector 32. (It will be appreciated that the output of the DMS filter may be detected off board, such as in a mass spectrometer or other detector, although the preferred practice is a shown.)

The DMS system is tunable, i.e., is adjusted to select ions of interest, by applying a perpendicular, DC tuning field, also referred to as compensation electric field or compensation voltage $V_C$, superimposed on the oscillating asymmetric RF field.

In preferred practice of the invention, the DC compensation (Vc) is superimposed on the RF field at the filter electrodes 20, 22, as will compensate the travel of a selected ion species in the ion filter. The compensation is selected or adjusted to allow specific ions that would otherwise be deflected towards one or the other of the electrodes to pass through filter 24 to the detector 32 without neutralization.

An exemplary detector 32 includes a top electrode 33 and a bottom electrode 35, and measures the charges deposited on the electrodes by the ion species. The electrodes can detect positively and negatively charged ions depending on the polarity of the voltage applied to the electrodes. simultaneously. Moreover, multiple ion species can be detected by using top electrode 33 as one detector and bottom electrode 35 as a second detector. Species detection and explosive identifications are made based on measuring the detected charges which are then associated with extant field conditions and applied compensation and this is then compared to historical data. A match of data enables identification of the detected ion species, such as TNT, DMNB, etc.

The system is controlled by a controller (not shown), which preferably includes an RF generator, a DC amplifier for applying the RF and compensation, as well as amplifiers for the detector electrodes, a data store, and an output or human interface.

It will be appreciated by persons skilled in the art that the motion of ions in an applied electric field can be expressed as a field-dependent ion mobility K with K=v/E, wherein v is the velocity of the ions and E is the applied electric field. K can be a function of the electric field E and the ion density N and can be written as K(E/N)=K(0)·[1+α(E/N)], wherein K(0) is the mobility for a specific ion at low voltages, and α is a parameter representative of the electric field dependence of the mobility K. Discrimination between different ion species can be determined by the difference in their mobility.

The electric-field-dependent mobility coefficient α(E/N) can define a unique mobility signature for the ion species which is device-independent. α(E/N) relates the size, effective cross-section, shape, and mass of the ion to the electric field conditions. It is understood that the increasing electric field tends to displace, stretch, and/or break the bonds of the ion, thereby inducing dipole, quadruple, or higher order moments of the ion. The functional dependence of α(E/N) on the electric field can be expressed as follows:

$$K(E/N)=K(0)\cdot[1+\alpha_2(E/N)^2+\alpha_4(E/N)^4+],$$

wherein $\alpha_i$ are ion-specific coefficients for even powers of the electric field E and N represents an ion density. Odd powers of E are absent since the absolute value of the velocity is independent of the electric field direction. As mentioned above, the effective electric field applied to the ions passing between the plates 22, 24 must be zero for the ions to reach the detector 32. Accordingly, the velocity impressed on the ions by the compensation electric field $V_C$ must be equal to the time-averaged velocity impressed on the ions by the asymmetric RF field 28. This yields the following equation for the compensation electric field $V_C$:

$$CV = \frac{\langle \alpha \cdot E_{RF}(t) \rangle}{1 + \langle \alpha \rangle + \left\langle \frac{d\alpha}{dE} \cdot E_{RF}(t) \right\rangle}$$

The value of the compensation electric field $V_C$ is hence related the α-parameter for the ion species, and the time dependence of the amplitude of the asymmetric RF waveform $E_{RF}(t)$. The relationship between differential ion mobility, compensation and the α-parameter, are described in more detail in commonly assigned U.S. patent application Ser. No. 10/187,464, which is incorporated herein by reference in its entirety.

Figure 1B:
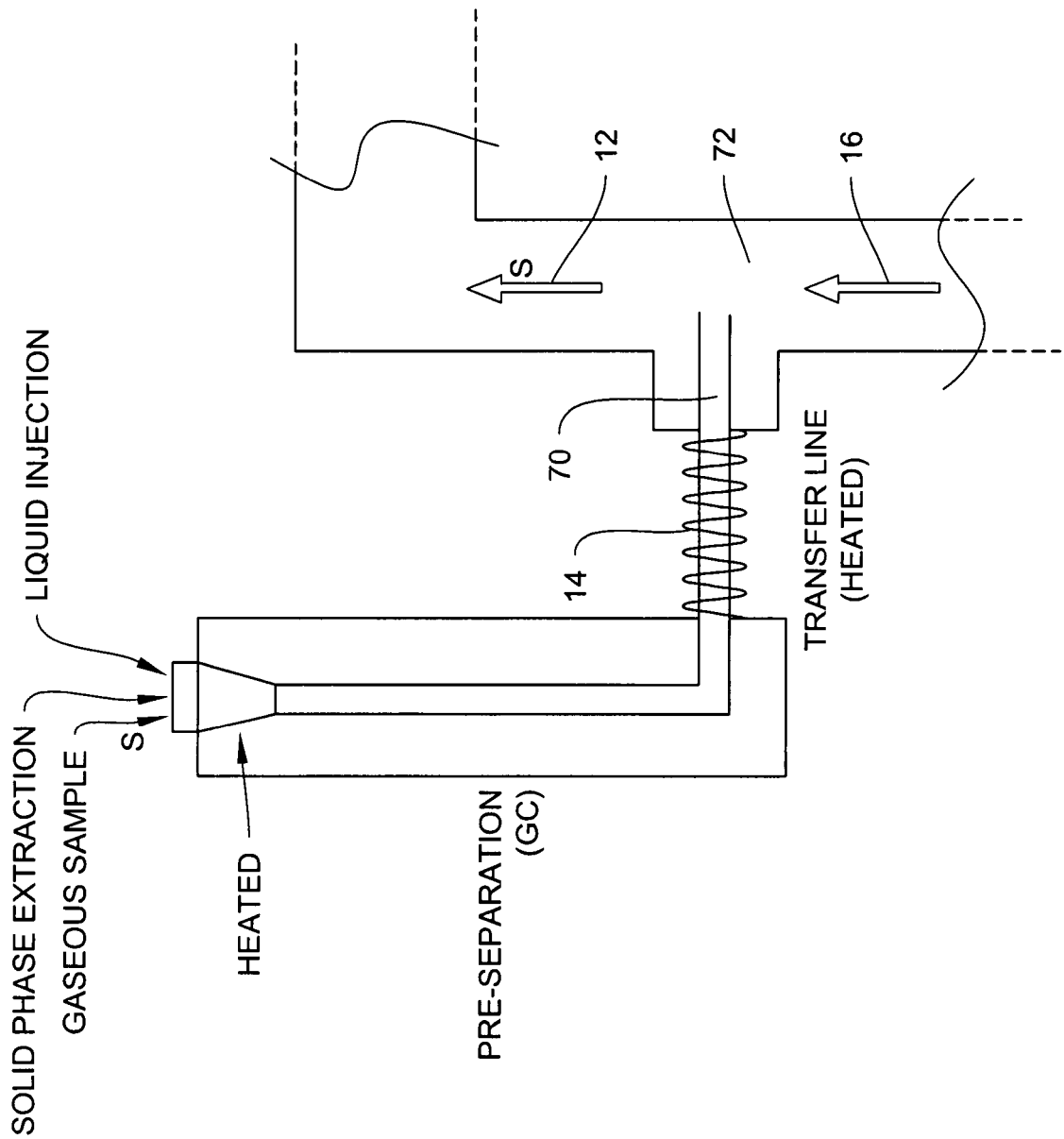

A scan of the compensation voltage $V_C$ provides a measure of all ions in the analyzer, and is referred to generally as differential mobility spectra (FIG. 1B). In the DMS spectrometer, the deflection of the ions along flow path 26 towards filter plates 20, 22, i.e., the ion separation is based upon $\Delta K = K_{High\_Field} - K_{Low\_Field}$ of the ions rather than on K alone, as seen with conventional low field ion mobility spectrometers.

We have found that an external parameter that can be used to improve the selectivity of the DMS analysis is moisture in the transport gas. Moisture is presumed to enhance ΔK by altering the level of cluster formation for the ion under the low field portion of the separation field. An enhancement of ΔK has been reported for $Br_2$ in the presence of polar molecules, such as water and acetone. However, although published studies of TNT with FAIMS (i.e., prior art DMS) did not show a shift in the compensation voltage with the sample's humidity, we have found that modification of the transport gas by addition of suitable dopants improves the detection capability of explosives by in DMS devices in practice of embodiments of the invention.

Embodiments of the present invention can provide rapid and accurate indications of explosives detections. In one embodiment, samples are drawn into the DMS flow path without a prefilter or alternatively using a membrane or other separator. The DMS device is compact and therefore dramatically reduces detection time. This device can also be beneficially used as a detector for a chromatographic separator, such as a Gas Chromatograph (GC)

An illustration is provided in FIG. 1B, where the GC capillary 70 delivers the separated eluent flow to the flow path at 72 and the eluent in turn is picked up in a transport gas (such as nitrogen or air) and is carried as an analyte carrying sample into the ionization region 74. The sample is ionized and proceeds as discussed herein.

In an illustrative practice of the invention, the ions travel at a desired velocity (e.g., around 6 meters per second for an ion filter 15 millimeters long, separated by a 0.5 mm gap). The gas flow velocity defines the ion velocity through the filter. The average velocity of the gas in the ion filter region can be defined as V=Q/A, where Q is the gas volume flow rate and A is the cross-sectional area of the channel. In one example, the DMS has a cross-sectional area A=5×10E-6 $m^2$. Therefore a flow rate of two liters per minute of gas is required to produce roughly 6 meters per second average velocity for the ions through the filter, for example.

The flow rates of the GC sample eluting from the column may be adequate for directly feeding into the DMS or may be assisted by use of a transport gas to augment the sample flow from the GC column. It will be appreciated by a person skilled in the art that by controlling the flow rate of the carrier gas in the GC column (or the ratio of carrier gas to sample) relative to the volume flow rate of the transport gas, various dilution schemes can be realized as desired. If the DMS must detect a high concentration of sample it is desirable to dilute the amount of this sample in a known manner so that the system operate in an optimal range of sensitivity without saturation.

Turning again to FIG. 1(A,B) it will be seen that a DMS of the invention is coupled to the GC preseparator. In order to obtain a fast response, we tightly control the dimensions of the DMS, and preferably provide a short flow path from the ionization side to the detection side of the ion filter section 24. While prior art concentric cylindrical DMS devices had achieved about a 10 second scan rate, devices of the present invention can run a complete spectral scan in one second and even in the millisecond range.

Prior art devices achieve dwell times on the order of 200 ms while devices of the invention can operate at about 1-2 miliseconds. Fast operating devices of the invention can have a residence time of at or around 2.5 milliseconds and less.

These prior art concentric cylindrical devices feature relatively long inner and our concentric cylinders, although a shortened concentric cylindrical device might be adapted for analyte detection. Nevertheless, a preferred embodiment includes a low-capacitance plate-type DMS design that enables rapid cycling and high DMS scan rates with reduced power requirements. These devices are operable with high RF fields, even in the low megahertz range and even up to five or even 10 MHZ, while the prior art concentric cylindrical DMS devices typically operate in the below megahertz range.

Preferred DMS devices of the invention have a gap defined between the filter electrodes 22, 24 of less than 1 mm and preferably 0.5 mm, and measure approximately a few millimeters width by about 15 millimeters in length. It is a feature of such design that the flow path 26 and ion filter 24 and preferably also the detector 32 are all formed on a supporting substrate, such as substrates 52 and 54 of FIG. 1A.

In a preferred embodiment, the ion filter is formed on insulating surfaces of the substrates. The benefit of being able to lay down electrodes on such insulating surfaces is that it lends itself to compact packaging and volume manufacturing techniques. As such, the ion filter is defined on these insulated surfaces by the filter electrodes, facing each other over the flow path, while the insulated surfaces of the substrates, such at region X, isolate the control signal at the filter electrodes from the detector electrodes 33, 35 to assure lower noise and improved performance.

It will be appreciated that embodiments of the invention include a GC-DMS invention with feature a multi-functional use of the DMS substrates. The substrates are platforms (or a physical support structures) for the precise definition and location of the component parts or sections of the DMS device. The substrates form a housing, enclosing the flow path with the filter and perhaps the detector, as well as other components enclosed. This multi-functional design reduces parts count while also precisely locating the component parts so that quality and consistency in volume manufacture can be achieved. The smaller device also has unexpected performance improvements, perhaps because of the shorter drift tube and perhaps also because the substrates also perform an electronic isolation function. By being insulating or an insulator (e.g., glass or ceramic), the substrates also can be a direct platform for formation of components, such as electrodes, with improved performance characteristics and reduced capacitance. The GC-DMS sensor with insulated substrate/flow path achieves excellent performance in a simplified structure. Sensitivity of parts per billion and possibly parts per trillion can be achieved in practice of the disclosed invention.

Moreover, by forming the electrodes on an insulative substrate, the ion filter electrodes and detector electrodes can be positioned closer together which unexpectedly enhances ion collection efficiency and favorably reduces the device's mass that needs to be regulated, heated and controlled. This also shortens the flow path and reduces power requirements. Furthermore, use of small electrodes reduces capacitance which in turn reduces power consumption. Quite favorably, depositing the spaced electrodes lends itself to a mass production process, since the insulating surfaces of the substrates are a perfect platform for the forming of such electrodes. This may be performed in a single chip-like electronics package.

It is further noted that use of the substrates as a support/housing does not preclude yet other "housing" parts or other structures to be built around and containing a GC-DMS device of the invention. Furthermore, it is possible to put a humidity barrier over the device. As well, additional components, like batteries, can be mounted to the outside of the substrate/housing, e.g., in a battery enclosure. Nevertheless, embodiments of the presently claimed invention stand over the prior art by virtue of performance and unique structure generally, and the substrate insulation function, support function, multi-functional housing functions, specifically, as well as other novel features.

It will be appreciated that in embodiments of the DMS device of the invention the substrates cooperate to form a device housing in that the substrates assist enclosing the flow path while also enabling mounting of the component parts. This multi-use, low parts-count housing configuration enables smaller real estate and leads to a smaller and more efficient operating DMS device, even smaller than 1"×1"×1".

Preferably the Spectrometer section 10 is formed with spaced insulated substrates 52, 54, (e.g., Pyrex® glass, Teflon®, pc-board) having the filter electrodes 20, 22 formed thereon (of gold, platinum, silver or the like). The substrates 52, 54 further define between themselves the input part (such as for receipt of sample S and transport gas 16) and output part (such as detector 32), along flow path 26. Preferably detector 32 has detector electrodes 33, 35 mounted on the substrate insulated surfaces 53, 55, facing each other across the flow path 26. It will be further appreciated that either insulating or conducting spacers 56 (FIG. 1C) serve to provide a controlled gap between electrodes 20 and 22 and define the enclosure of the flow path. The spacers may be formed by etching or dicing silicon wafers, but which may also be made of patterned Teflon, ceramic, or other insulators. These spacers may be part of the substrates forming a complete sidewall 56' or may be separate elements, such as layers 56, 56 and even may form electrodes 56e, 56e for heating the flow path or for confining the ion flow with an electric field. This confinement can result in more ions striking the detectors, and which in turn improves detection. Optionally a heating element 57 is associated with at least one of the substrates 54, as shown in FIG. 1A.

Figure 1C:
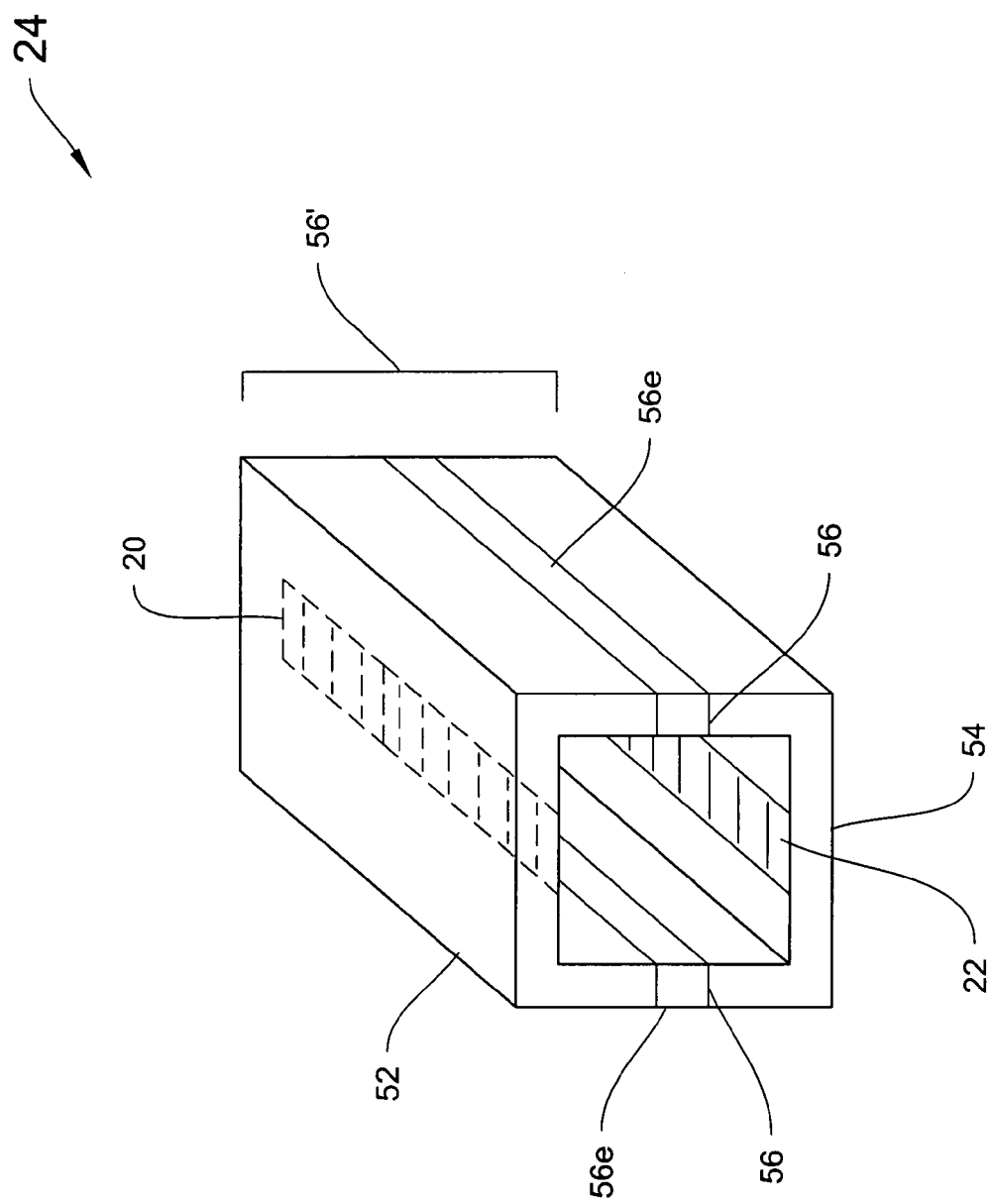
Figure 1D:
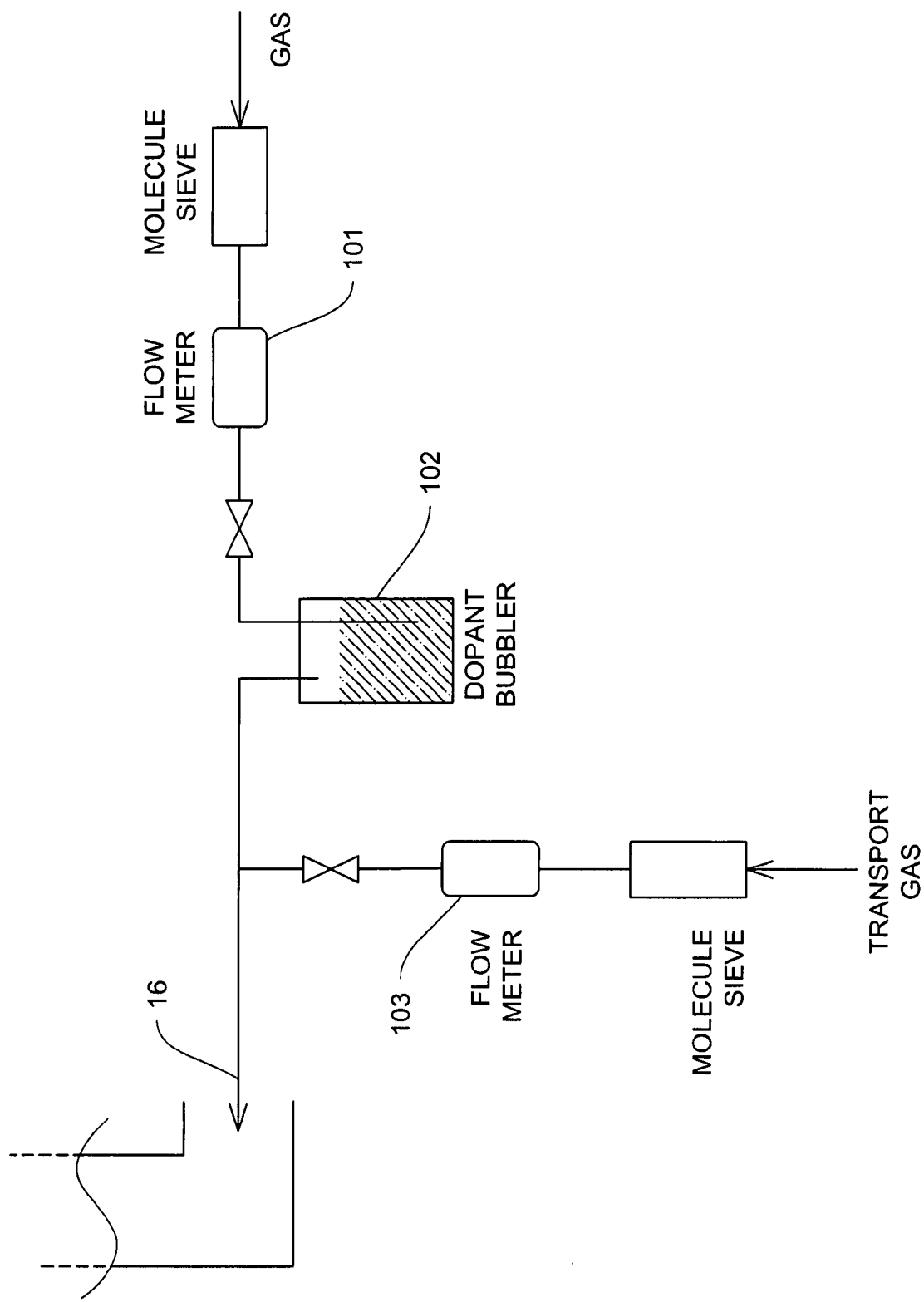

As shown in FIG. 1C, the electrodes 20, 22 of filter 24 are preferably formed on the inner walls substrates 52, 54, but also with an area of exposed substrate remaining. Therefore the active area of the electrodes is kept small and keeps the capacitance low. As well, with reduced volume of such a compact "micro-machined" device, an efficient and fast operating DMS is provided. It is a preferred characteristic of the invention that the flow path 26 along its sides at least in the ion filter 24 is enclosed by the substrates alone or in cooperation with the filter electrodes and the spacers. The spacers effectively define the electrode separation, i.e., the analytical gap separating the electrodes in the ion filter 24. This compact design enables fast and reliable DMS operation and can be favorably employed in practice of embodiments of the invention.

In operation of the DMS spectrometer some ions will be driven into the electrodes 20, 22 and will be neutralized. These ions can be purged by heating. This may be accomplished in one embodiment by heating the flow path 26, such as by applying a current to filter electrodes 20, 22, or to spacer electrodes 56, 56. As heater electrodes, they also may be used to heat the ion filter region to make it insensitive to external temperature variations.

Pump 39 generates flow, such as exhaust 39, in the compact structure housing/substrate structure, and may also be used for recirculation for supply of conditioned transport gas (such as dry air) to the input part or even recirculation of the neutralized detected ion species for redetection.

The devices of the invention have various electrode arrangements, possibly including pairs, arrays and segments. Filtering may include the single pair of filter electrodes 20, 22. But device performance may be enhanced by having a filter array 62 having a plurality of ion filters 24*a-n*, each of which may have its/their own operating environment and including own assigned dopant introduction, which even better detection control and performance. It will be appreciated that it is possible to have multiple filters 24 in a serial array in a single flow path or with multiple parallel filters in multiple parallel flow paths, each with at least one assigned filter or an array.

Figure 1E:
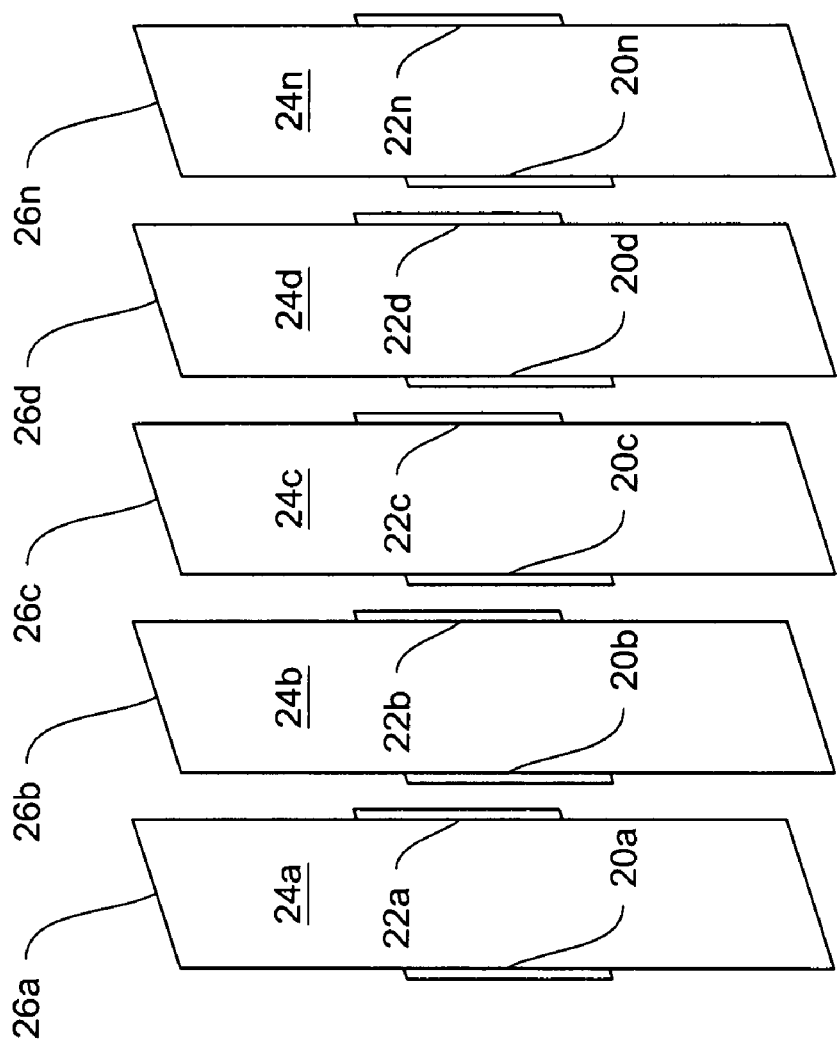

The filter array 62 of FIG. 1E has a plurality of paired filter electrodes 20a-n and 22a-n and may simultaneously pass different ion species by control of the applied signals for each electrode pair. In addition, it is possible to sweep the control component for each pair over a voltage range for filtering a spectrum of ions.

Further, with an array of filters, a complete spectral range of compensation voltages can be more rapidly scanned than with a single filter. In an array configuration, each filter can be used to scan over a smaller voltage range. The combination of all of these scans results in sweeping the desired full spectrum in a reduced time period. If there are three filters, for example, the spectrum can be divided into three portions and each is assigned to one of the filters, and all three can be measured simultaneously.

In another mode, filter array 62 may include the pairs of filter electrodes 20a-e and 22a-e and may simultaneously enable detection of different ion species by applying a different compensation bias voltage to each filter of the array, without sweeping. In this case, only an ion species that can be compensated by this fixed compensation voltage will pass through each filter, and the intensity will be measured. This dedication to a particular analyte of interest can be greatly enhanced by selection of a species-specific detection-enhancing dopant associated with improved detection of that species. In practice of the invention, array 62 may include any number of filters depending on the size and use of the spectrometer.

Therefore, as will be appreciated by those skilled in the art, different species have different affinities to different dopants, and therefore in practice of an embodiment of the invention having an array of electrodes, multiple flow paths can be provided and each flow path can be doped with a different dopant. The result is that the ion filters and detectors can be specialized for a selected species and now further specialization of the flow paths result in enhanced discrimination capability.

Use of arrays is important when there is a desire to measure perhaps a dozen or so compounds in a very short amount of time. If a fast GC is used as the front end to a such as preferred compact and fast DMS of the invention, multiple scans can be performed within a single GC peak. Therefore a complete characterization of a GC peak can be performed in a single DMS filter of the invention in an array of such filters for simultaneous detection of all the constituents in the given GC peak.

We have achieved excellent species discrimination by use of dopant in the DMS system. In the context of this application, doping is broadly defined as the process of adding an analyte for the purpose of affecting ion species behavior. Doping may include the step of addition of an analyte in the ionization process whose ionization releases free electrons which enables ionization of negative species. Doping may include the step of use of an additive to improve ionization efficiency. Doping may include the step of addition of an analyte that affects species behavior and causes peak shift.

Figure 2:
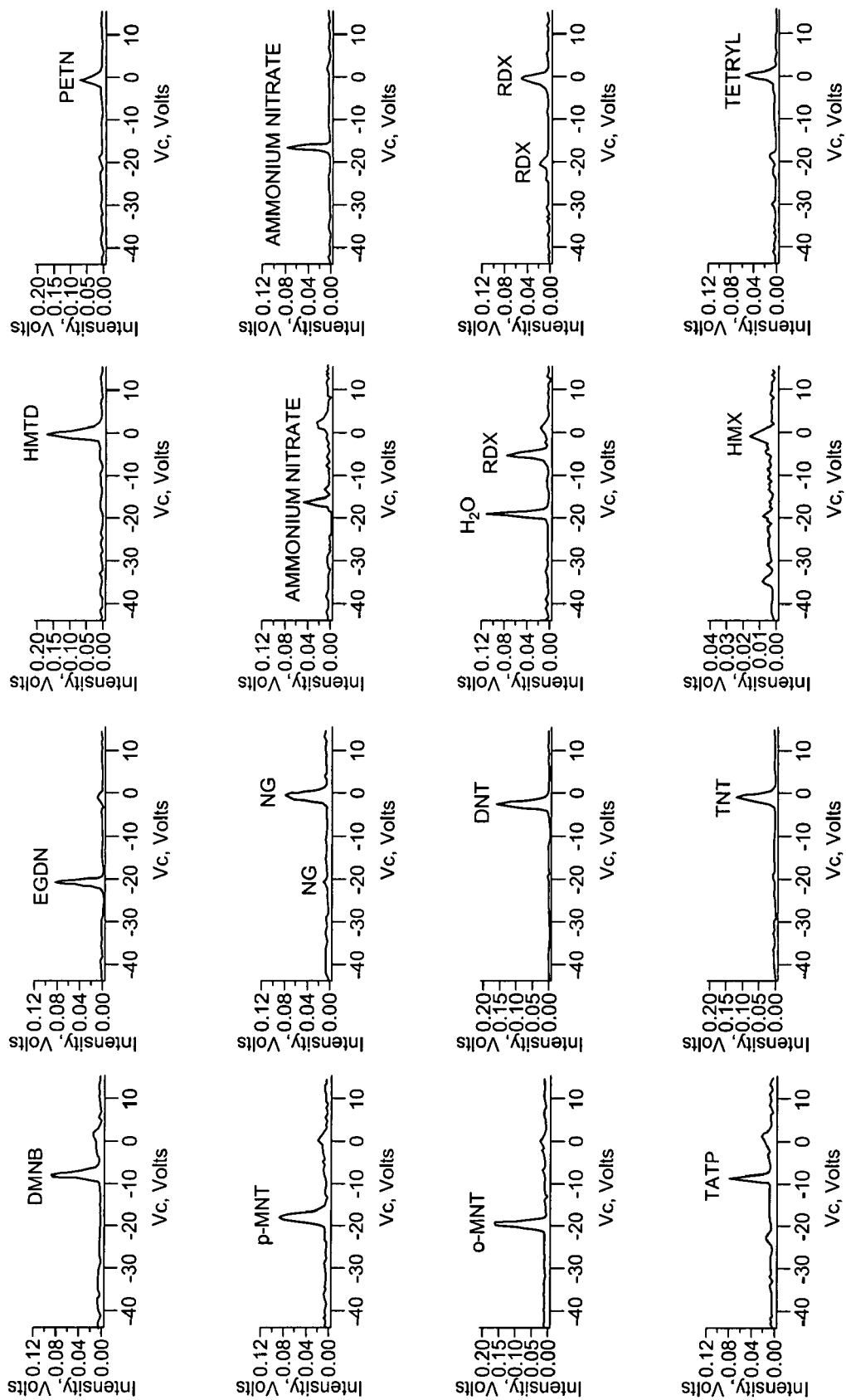
FIG. 2 shows detector signal strength versus compensation voltage $V_C$ for several detected ions without dopant addition in practice of an embodiment of the invention.

Referring back to FIG. 1A,B, the illustrative DMS spectrometer of the invention is interfaced with a gas chromatograph (GC) in which a gaseous sample or and liquid sample, such as a solution containing an explosive to be analyzed, is injected. The sample is transported through the GC and emerges after an elution time RT at the output of the GC where it is injected via a heated transfer line 14 into a transport gas flow 12. The transport gas flow 12 may also include a dopant flow 16, as depicted in FIG. 2. The dopant can be supplied by flowing a gas, such as $H_2$, $N_2$, Ar, He and the like, through a bubbler (FIG. 1D) containing the dopant in liquid or solid form, or the dopant can be stored in gaseous form in a gas tank and enter the transport gas stream at a predetermined rate through a controlled leak. It will be understood that the flow rates of the transport gas and the dopant can be controlled by employing flow meters known in the art.

The DMS can operate under atmospheric pressure, thereby reducing the need for a pump, but may also be operated at reduced pressure for some species of interest, where reduced pressure can improve the sensitivity and resolution of the instrument. FIG. 8 shows detection of TNT, DNT, NG and EGDN in practice of the invention at 0.5 atm at 120° C. Compared to operation at 1 atm, the peaks shifted 5 volts on the Vc axis, which is a tool that enables shifting of peaks in a cluttered sample or away from interfering peaks, or even offset from the background spectra (RIP).

In the experiments described below, an illustrative DMS analyzer was operated using specialized electronics containing separation waveform generator, a compensation voltage amplifier, and two-polar electrometer (for the detector). The separation waveform generator was based on a soft-switched, semi-resonant circuit that incorporated a fly-back transformer and allowed variable peak-to-peak amplitudes of the asymmetric waveform from 200V to 1600V without altering the waveform shape. The operating frequency of the generator was 1.3 MHz and the amplitude was between 950 and 1200V. A compensation voltage amplifier was controlled by data collection software and was scanned between 30 to –10 V in ~1 sec periods. Two Faraday plate detectors floated 5 V± provided simultaneously detection of positive and negative ions (modes) during one scan of the compensation voltage. Signal was processed to digitize and store spectra for every scan. Conventional software was used to control DMS hardware, to collect DMS spectra, to save data and to display the results.

An Agilent model 6890A gas chromatograph modified with an ANTEK μWave GC 3600 (Rev. 1.044-01) was used. Several columns were used, including a carbon coated 5 m capillary column with OV-1 bonded stationary phase. Conditions of operation included: initial temperature, 100° C.; initial time, 0 min; temperature ramp, 25° C./min; final temperature, 200° C.; and final time, 2 min. The split ratio for the injector was 30:1 and injector temperature was 100° C. Carrier gas was nitrogen at 0.5 ml/min.

Table 1 is a listing of common names and chemical names of exemplary explosive chemicals that may be detected in practice of the invention.

TABLE 1

| Common name | Chemical Name |
| --- | --- |
| NT | 2-nitrotoluene |
| NT | 3-nitrotoluene |
| NT | 4-nitrotoluene |
| TNT | 2,4,6-trinitrotoluene |
| DNT | 2,4-dinitrotoluene |
| DNT | 3,4-dintrotoluene |
| DNT | 2,6-dinitrotoluene |
| EGDN | ethylene glycol dinitrate |
| NG | nitroglycerine |
| RDX | cyclotrimethylenetrinitramine (cyclonite) |

TABLE 1-continued

| Chemical Name | |
|---|---|
| PETN | pentaerythritol tetranitrate |
| HMX | homocyclonite (octogen) |
| NH4NO3 | Ammonium nitrate |
| NitroBid Formulations | 1,2,3-propanetrial trinitrate |
| C-4 | RDX &/or PETN |
| Semtex | RDX &/or PETN |
| Detasheet | RDX &/or PETN |
| Dynamites | EDGN &/or NG |

Table 1

In one set of experiments, the following explosive compounds were analyzed in practice of the invention as 1000 μg/ml solutions in acetonitrile: 4-nitrotoluene (NT); 2,6-dinitrotoluene (DNT); 2,4,6-trinitrotoluene (TNT); 4-nitrobenzene (NB); 1,3-dinitrobenzene (DNB); 1,3,5-trinitrobenzene (TNB); 1,3,5-triazine, hexahydro-1,3,5-trinitro (RDX); 1,2,3-propanetriol, trinitrate (NG); and pentaerythritol, tetranitrate (PETN). Working solutions were prepared by serial dilutions in acetonitrile with concentration of ~10 μg/ml. In the GC/DMS studies, retention times were determined for individual chemicals prior to any studies. Vapors of water, acetone, methylene chloride, methylene bromide, methanol and propanol were used as exemplary dopants for modifying the transport gas. The range of dopant concentrations investigated was 0 to more than 10,000 ppm of dopant in transport gas.

In one practice, stock solutions of individual explosives were characterized to determine retention times and compensation voltages for each substance. In these studies, 2 μl of the working solution were injected with a split ratio 30 so mass of chemical delivered to the GC column was in sub-nanogram range. The injected mass was adjusted to yield a near Gaussian shaped chromatographic peak with width of 2-5 s. The DMS analyzer was operated continuously and mobility spectra were obtained every second. Since the widths of individual GC peaks were ~2-5 s at baseline during an elution profile, two to five differential mobility spectra were recorded for each explosive throughout a range of concentrations. All differential mobility spectra were saved and post-analysis processing of data was used for graphic analysis.

To obtain field mobility dependence for ions of explosives, mixture of explosives were used with GC-DMS analysis and amplitudes from 950 to 1300 V for the separation voltage. These studies allowed extraction of the dependence of the compensation voltage $V_C$ vs. separation voltage for each peak in the differential mobility spectra. Standard procedures were used to derive alpha ($\alpha$) functions.

Exponential dilution was used to generate response curves and to determine limits of detection for the explosives. In this method, a known amount of an explosive was injected into a 0.5 L heated round bottom glass flask providing calculated concentrations in the gas flow (transport gas). Vapor concentrations of explosives decreased exponentially according to $$c(t) = c_0 \cdot \exp\left(-\frac{tQ}{W}\right)$$

where $c_0$ is initial concentration; W is volume of exponential dilution flask; Q is carrier gas flow rate regulated by a flow controller; and t is time. The gas flow was then delivered to a DMS analyzer through heated lines to minimize adsorption of sample on the tubing. Temperatures needed for explosives to obtain gas concentrations without adsorption or thermal decomposition ranged from 100 to 240° C. and were compound specific.

As mentioned above, dopants can be introduced from a solid, liquid or gaseous source. In one design, a vapor generator was used to provide constant concentration of modifying chemical into the transport gas for GC DMS studies. The vapor generator included a saturated vapor source, under temperature control, and a source of purified gas, e.g. air. Flow controllers were used for controllably mixing the gas containing the dopant with the transport gas.

In further practices of the invention, we can detect explosive materials per se, without a dopant, as shown in FIG. 2. Differential mobility spectra for nitrated aromatic compounds and explosives in purified air are shown in FIG. 2 for compensation voltages from −40 to 10 V with a separation voltage (field) of 950 V (~20 kV/cm). The DMS operated at atmospheric pressure without added dopant. The detected ions were either positive (o-MNT, p-MNT, DMNB, TATP, HMTD), negative (HMX, Tetryl, PETN, RDX, TNT, DNT, NG, EGDN), or both positive and negative (RDX, AN). Little fragmentation had occurred apart from a barely discernible peak for NG (at −20 V) and peaks of low intensity for PETN and RDX (also at −20 V). This implied a high stability of product ions for explosives and is consistent with prior studies for traditional mobility spectrometers where little fragmentation was observed through ionization in air at ambient pressure. Product ion peaks in DMS spectra, as seen in FIG. 2, suggest that the product ion intensity is concentration dependent but that ion identity, seen in the compensation voltage, is independent of concentration.

We can also selectively improve peak separation (resolution). Resolution of ions in DMS arises through differences in mobilities under high and low field conditions in the asymmetric RF field, which can be enhanced by the formation of cluster ions during the low field portion of the separation field. This was quantitatively noted for moisture with organophosphorous compounds and could be associated with collisional frequencies between ions and water molecules to form water clusters during the 120 ps RF field period. At the high voltage RF field period, the ions would be desolvated providing a difference in mobility.

Figure 3:
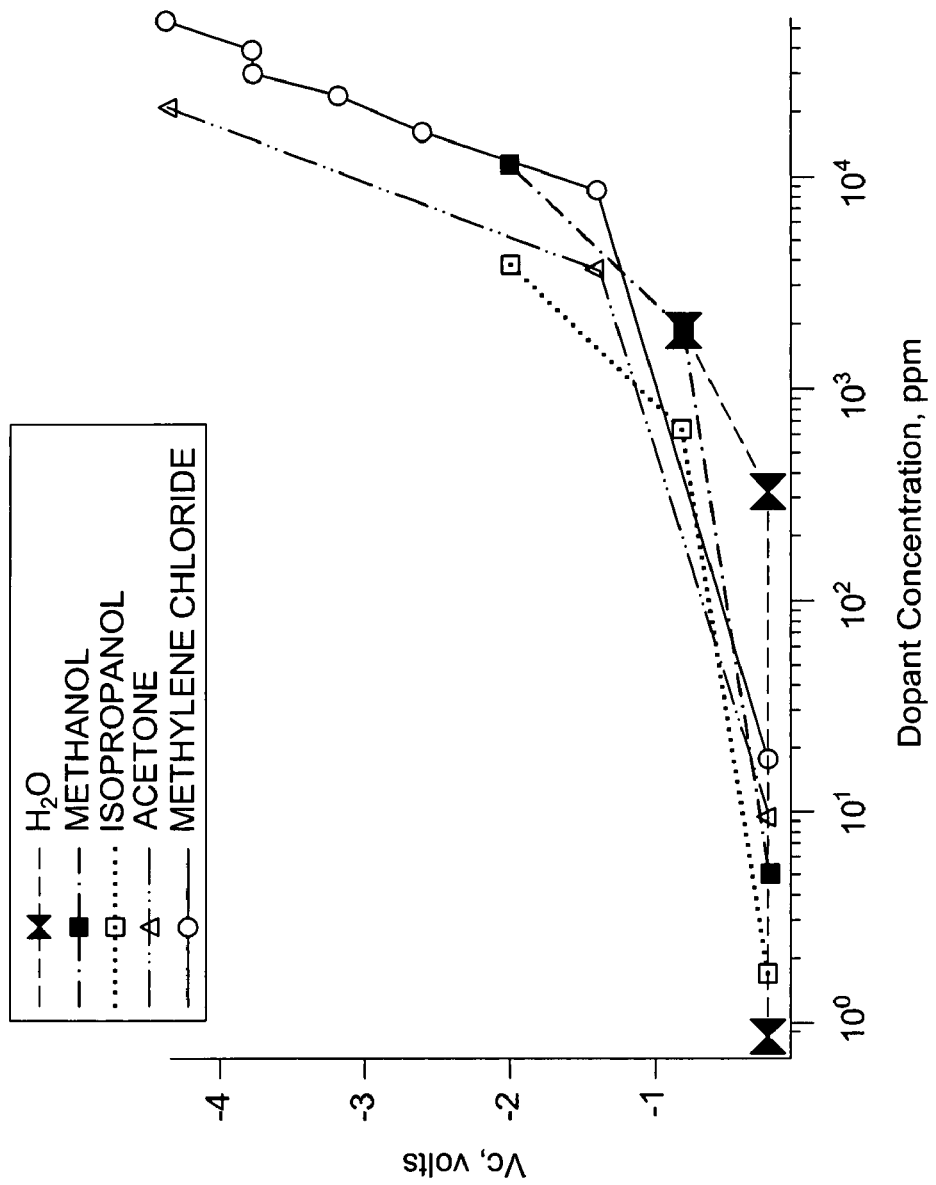
FIG. 3 shows the observed increase in the compensation voltage VC for TNT with increasing concentration of several dopants in practice of an embodiment of the invention.
Figure 4A:
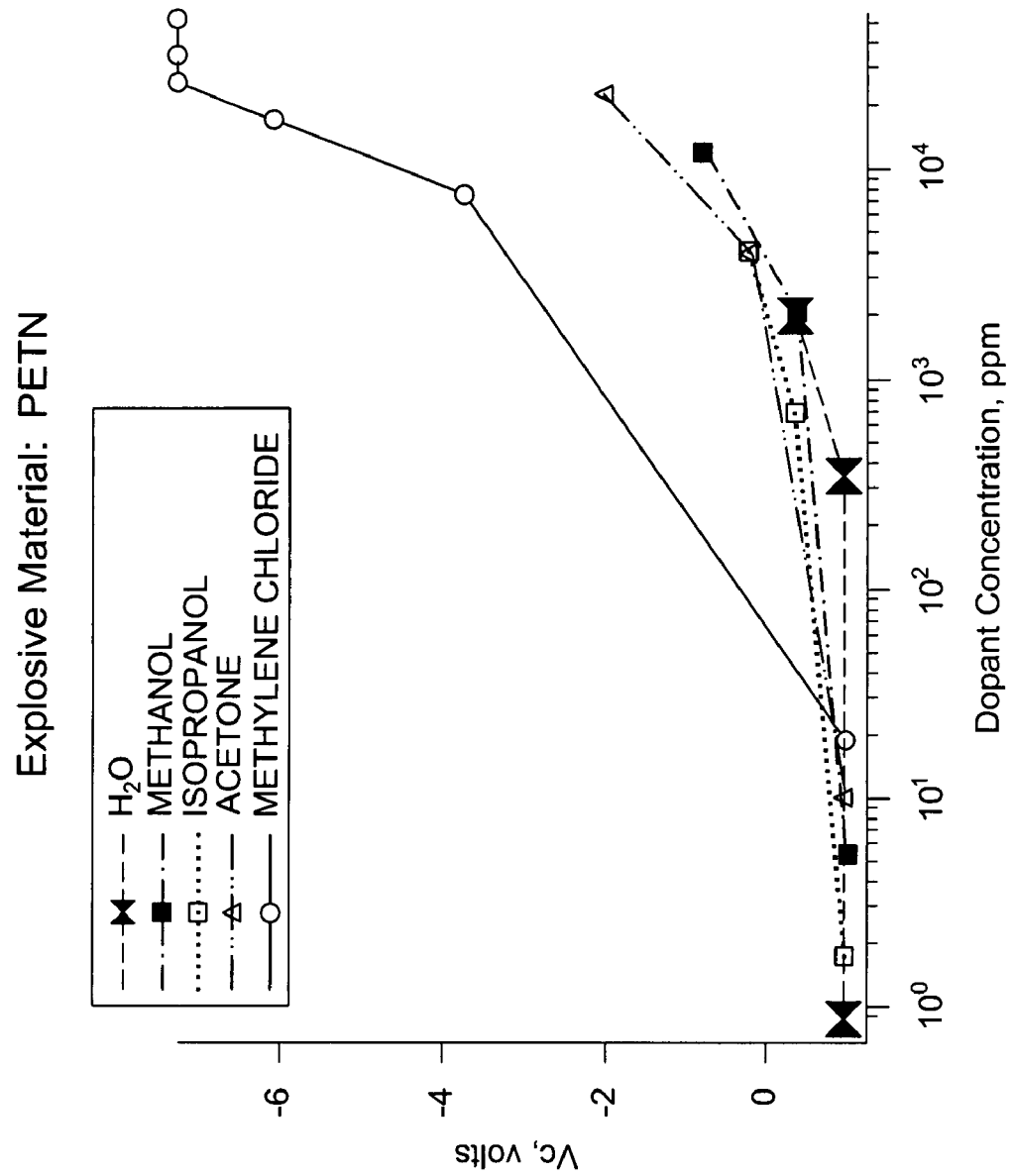
FIGS. 4A and 4B show the observed increase in the compensation voltage VC for PETN with increasing concentration of several dopants in practice of an embodiment of the invention.
Figure 4B:
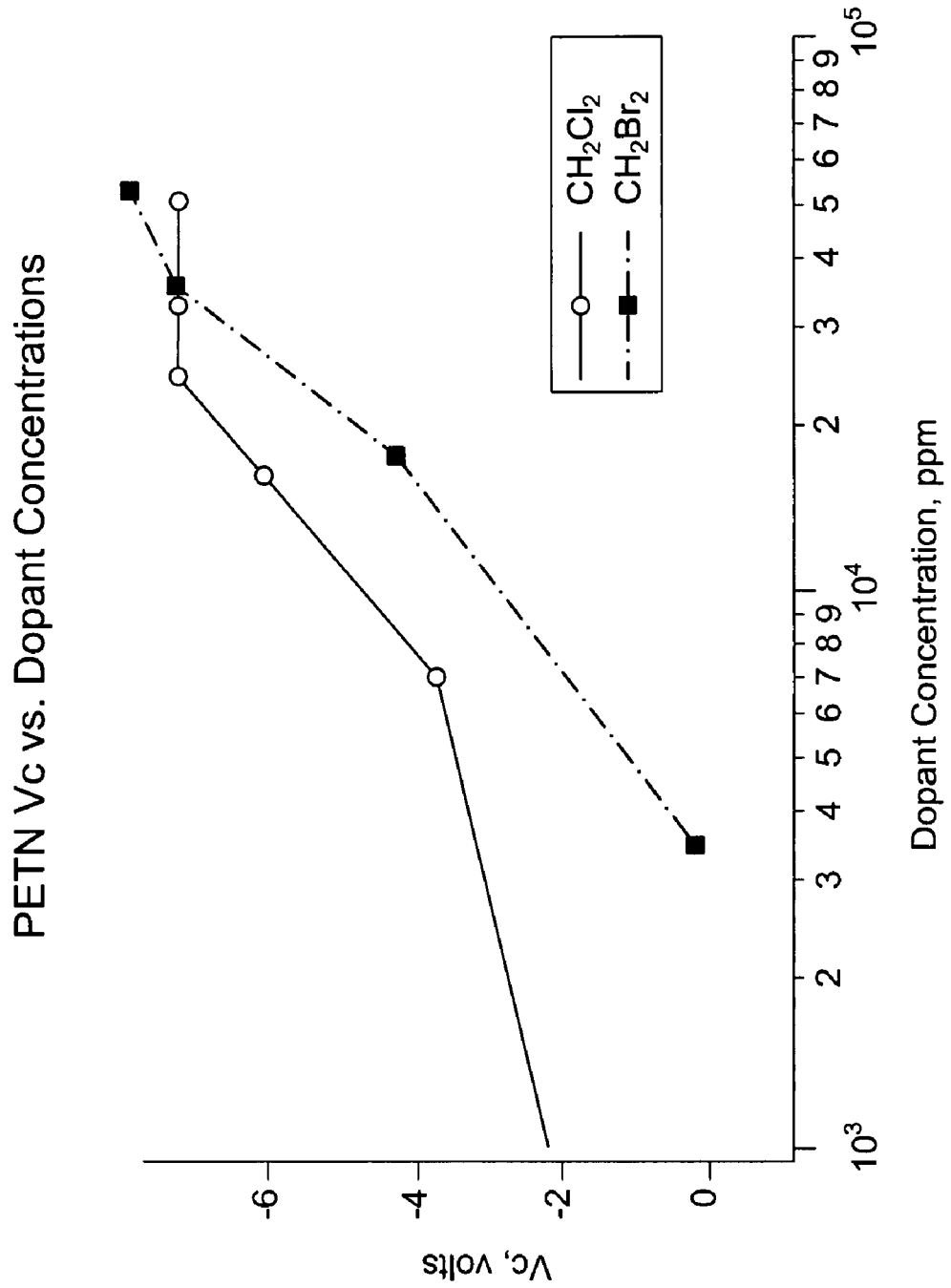

In FIG. 3, the influence of various dopants, such as $H_2O$, methanol, isopropanol, acetone and methylene chloride, on the compensation voltage for DNT is shown. As seen in FIG. 3, the addition of acetone and methylene chloride in concentrations of approximately 3,000 to 10,000 ppm causes a dramatic increase in the compensation voltage $V_C$ for DNT. As seen in FIGS. 4A and 4B, other explosives, in this case PETN, respond differently to the same dopants. For PETN, only methylene chloride and methylene bromide (FIG. 4B) cause a significant increase in $V_C$. A change in the compensation voltage therefore depends on a combination of the explosive substance and the dopant species and cannot be estimated in advance.

As mentioned above, the compensation voltage and the $\alpha$-values that characterize the field-dependent mobility are related, so that the $\alpha$-values can be determined from a measurement of $V_C$.

Figures 5A, 5B:
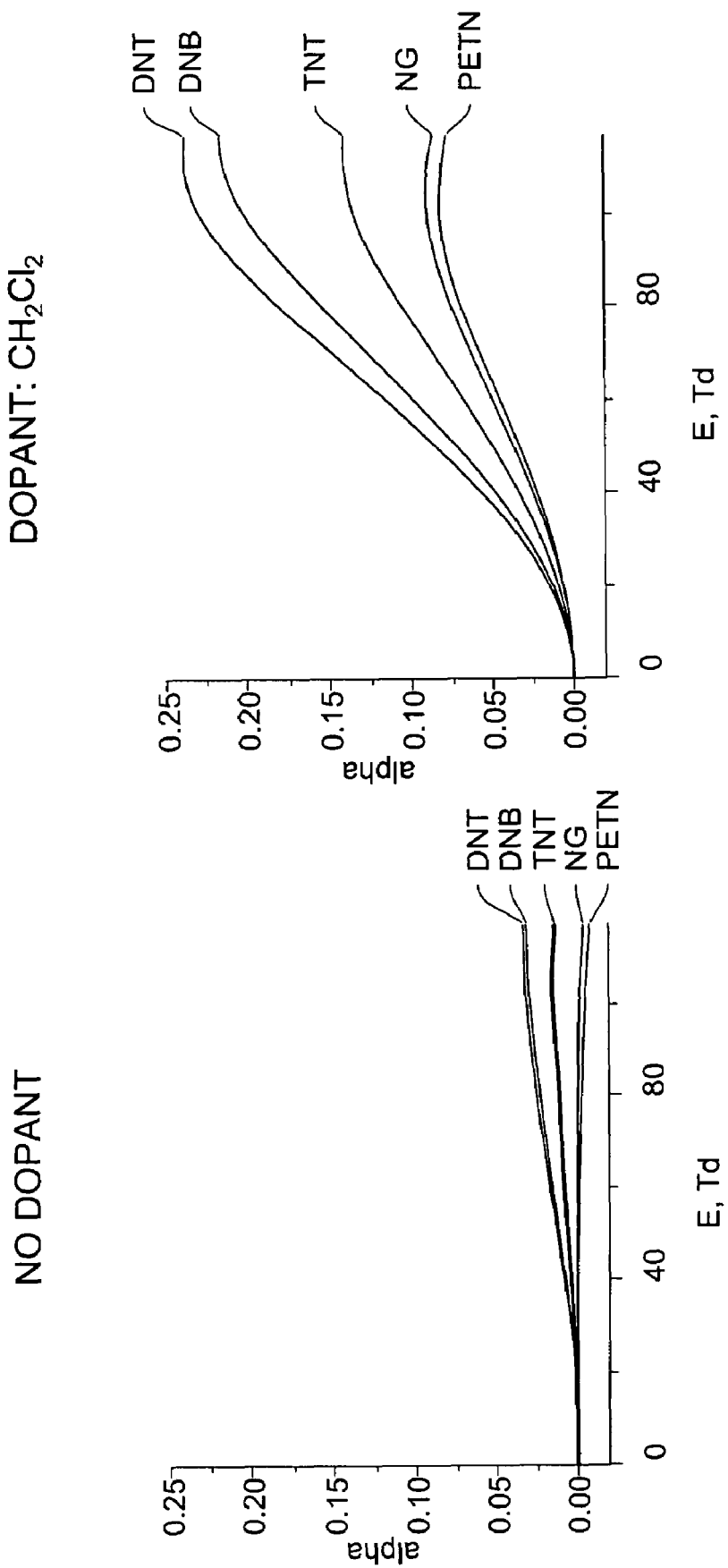
FIG. 5A shows a graph of the electric field dependence of alpha (α) for several explosives without addition of a dopant in practice of an embodiment of the invention.
FIG. 5B shows a graph of the electric field dependence of alpha (α) for the explosives in FIG. 5A with addition of a $CH_2Cl_2$ in practice of an embodiment of the invention.

FIGS. 5A and 5B shows graphs of a versus E/N for explosives at 0.1 ppm moisture in air at 150° C. The greater the $\alpha$-value, the greater the potential for ion resolution through mobility differences at high and low fields. In FIG. 5A, the $\alpha$-function is plotted for experimental conditions where no dopant was added. The difference of $\alpha$ between low and high electric field conditions is only −0.005 to 0.02. This is less than half the values obtained for ketones (from acetone to octanone) which have α-values between 0.05 and 0.1. These graphs are the first reported graphs for negative ions. The results suggest that best ion separation will occur with E/N values of ~120, corresponding to an electric field of 1200 V/cm at 660 Torr ambient pressure.

Turning now to FIG. 5B, the addition of methylene chloride ($CH_2Cl_2$), chosen on the basis of the observed shift of the compensation voltage $V_C$ with dopant concentration plotted in FIGS. 3, 4A and 4B, causes a dramatic change in the α-functions. The differential mobility spectra for explosives with approximately 1000 ppm methylene chloride in air in the gas flow shown in FIG. 5B may be directly compared to the plots shown in FIG. 5A. The presence of the dopant-modified vapor has caused either a change in the ion identities or in the ion behavior in the analyzer. Changes in the vapor concentration of the explosives cause no change in the compensation voltage of the ions or changes in DMS spectra. However, mass spectra (not shown) showed nearly complete replacement of $O_2^-(H_2O)_n$ with $Cl_2^-(H_2O)_n$ for the reactant ions. Reaction chemistry may be partially responsible for some of the changes in DMS spectra. For example, mass spectra demonstrated that chloride ion caused the formation of $M·Cl^-(H_2O)_n$ for NG replacing $M·NO_2^-$ as the primary ion. Thus, in the DMS scan, new peaks may arise from $M·Cl^-(H_2O)_n$ and hydride abstraction in the drift tube, rather than in the DMS/MS (mass spectrometer) interface. Similarly, the mass spectrum for PETN was largely comprised of fragment ions and was consistent with peaks near 12 V in the DMS spectra. Fragments in the mass spectrum supported fragmentation in the differential mobility spectrum for TNT. Those ions most dramatically affected by addition of methylene chloride in the transport gas showed little if any discernable differences in mass spectra. It may therefore be inferred that the ion was present as two different species, depending on the applied electric field:

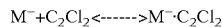

Ion at High Field Ion at Low Field

Consequently, the differences in mobility (ΔK) between the unclustered and clustered ions should be high and a large compensation voltage would be needed to guide the ion through the filter region of the FAIMS. It should be noted that there is no indication that the chemical, i.e. the exemplary explosives, are fragmented by the addition of chloride. This specific example of vapor modifiers in the transport gas of a differential mobility spectrometer may represent general possibilities for improved ion separation.

Returning now to FIG. 1, an illustrative GC-DMS spectrometer 10 of the invention includes a gas chromatograph (GC) as a pre-separation stage. The combination of gas chromatography with DMS is understood to have several advantages. The pre-separation step adds retention behavior to compensation voltage for enhanced specificity, and the introduction of constituents as single constituents or an elution peak with a few compounds increases the reliability of APCI reactions. Results from GC/DMS determinations of explosives in a mixture are shown in FIGS. 6A-6C where only air is used as the transport gas. The spectra were taken with the DMS operating at atmospheric pressure.

Figure 7:
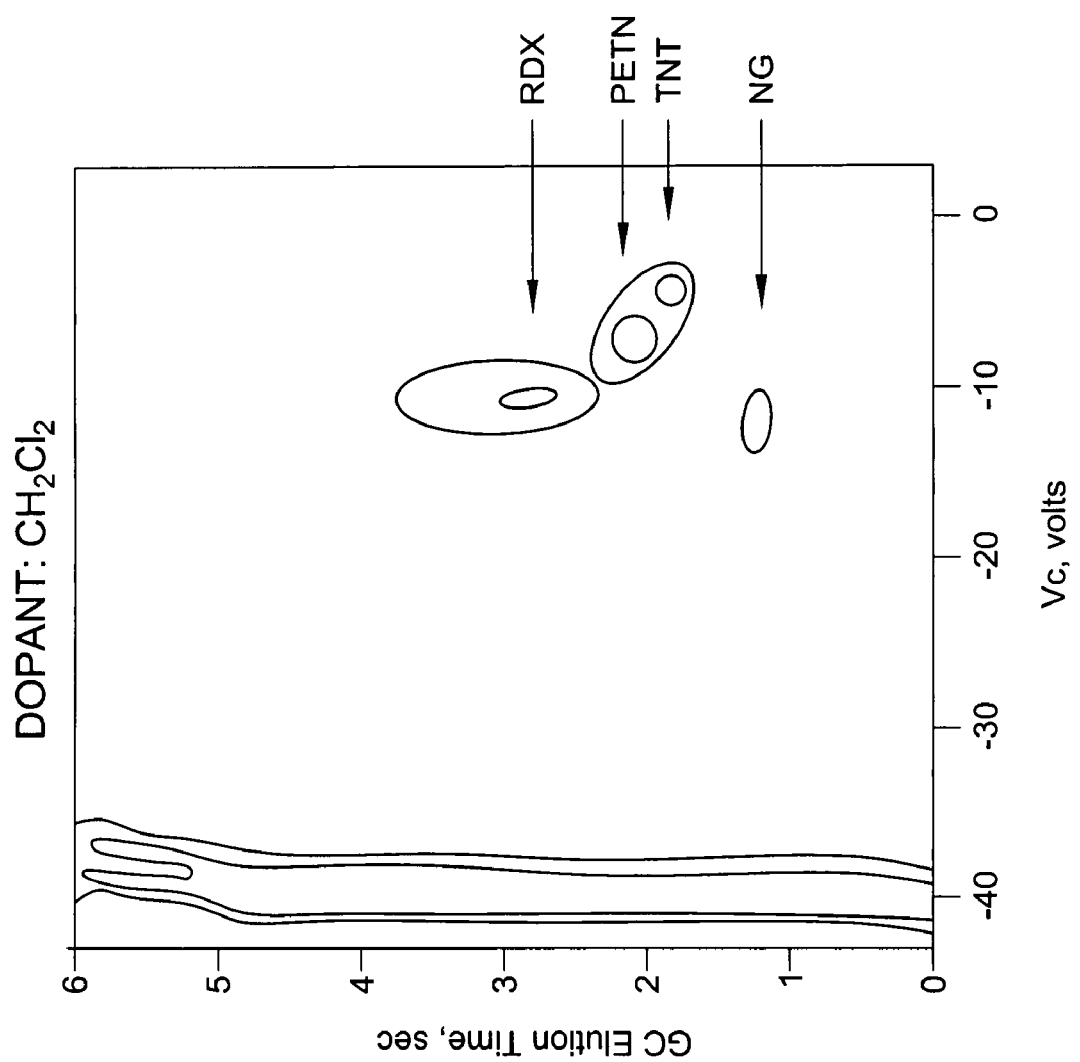
FIG. 7 shows DMS spectra for the mixture of FIG. 6B obtained by coupling a fast GC with elution time on the order of 2-3 seconds to a fast DMS in practice of an embodiment of the invention.

FIG. 6A shows a contour plot of the DMS response for a mix of RDX, PETN, TNT and NG without an added dopant. There is chemical resolution in the vertical axis (chromatographic elution time), but limited separation in the horizontal axis (compensation voltage $V_C$ or ΔK). The addition of 1000 ppm methylene chloride ($CH_2Cl_2$) dopant in the transport gas (see FIG. 6B) significantly enhances the signatures of RDX, PETN, TNT and NG DMS spectra. As seen in FIG. 6C, an even more profound effect is observed when chloroform ($CHCl_3$) is added as dopant. FIG. 7 shows DMS spectra for the mixture of FIG. 6B obtained by coupling a fast GC (with elution time on the order of 2-3 seconds) to the fast DMS, where the intensity peaks associated with the four explosive constituents RDX, PETN, TNT and NG are clearly discernable for a GC with a 2 second retention time.

It will be appreciated that in practice of embodiments of the invention, the response time and overall analytical performance of a DMS for explosives can be assisted by selection of suitable dopants with a GC pre-separator. However, it will also be appreciated that a GC pre-separator is not required for detection of explosive-related ion species in alternative practices of the invention. It will be further appreciated that in practice of embodiments of the invention, that DMS spectra for specific explosive and dopant combinations depend on several variables, such as Vrf and Vc as well as transport/flow rate and pressure in the flow path. FIG. 8 shows DMS spectra at 0.5 atm pressure for detection of ionized explosives analytes for TNT, DNT, NG and EGDN which can be compared to the 1 atm spectra of FIGS. 6A-C. In this example, lowering the pressure shifts the peak position, which is indicated in changes in the required compensation voltage Vc, compared to the 1 atm data.

Although the spectra of FIGS. 6A-C and FIG. 7 are only shown for negative mode detections, it will be understood by those skilled in the art that positive mode detections may have valuable data for those substances (i.e., a particular analyte may be indicated by formation of both positive and negative species, according to the signature characteristics of the ionized analyte).

Figures 8A, 8B:
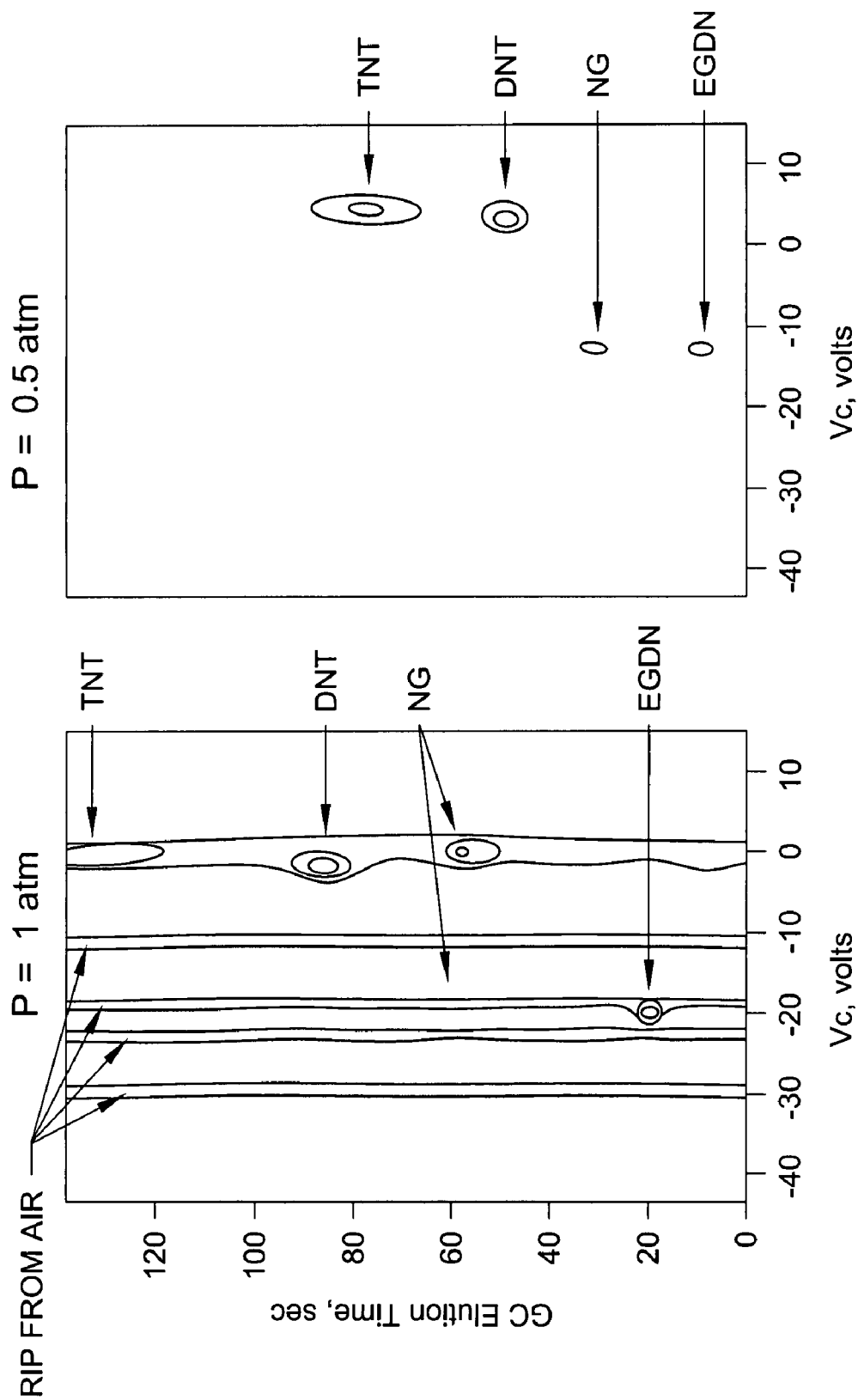
FIG. 8A-8B shows reduced pressure (0.5 atm) response (A) of DMS spectra for several explosives compared to spectra at 1 atm (B)

FIGS. 8A-8B show reduced pressure response for a DMS system of the invention (0.5 atm) for several explosives compared to spectra taken at 1 atm. The left-hand frame (A) shows background spectra (RIP) from ionization of the carrier gas (air) at 1 atm and interference with detection peaks for TNT, DNT, NG, and EGDN. However, we can favorably reduce this competition by reducing pressure in the device. While this adjustment is not always required, in this example it can be seen in the right-hand frame (B) that the same species now detected at 0.5 atm are separated from the RIP. This results from a differential shift from these changed conditions, wherein the analytes of interest have shifted to compensation at a higher Vc by about 5-10 volts and the RIP spectra have shifted so much as to be off scale. Now the explosives spectra can be more easily analyzed with more reliable identifications being possible.

FIG. 9 is a Table listing illustrative DMS detections for several combinations of explosives/taggants without and with addition of dopants. Four dopants were used in the experiments: methyl bromide ($CH_2Br_2$), methyl chloride ($CH_2Cl_2$), methanol ($CH_3OH$), and isopropanol. The following explosives were investigated were investigated: HMX, Tetryl, PETN, RDX, NG, TNT, EGDN, DNT, o-MNT, p-MNT, DMNB, TATP, HMTD and AN. For an explanation of the used abbreviations, see Table 1. FIG. 9 shows performance related to ion species (negative or positive), the measured compensation voltage(s) $V_C$, as well as experimental conditions. Rf denotes the peak-to-peak amplitude in the DMS filter. As seen in FIG. 9, HMX, Tetryl, PETN, RDX, and NG were detected as having identifiable detection peaks in the negative mode with four dopants. TNT and EGDN were detected in the negative mode with $CH_2Cl_2$, $CH_3OH$, and isopropanol, but not with $CH_2Br_2$. DNT was detected in the negative mode with $CH_3OH$ and isopropanol, but not with $CH_2Br_2$ and $CH_2Cl_2$. o-MNT, p-MNT, DMNB, TATP, and HMTD were detected in the positive mode having minor $V_C$ shifts.

It is an advantage of the preferred embodiment that positive and negative mode detections can be obtained simultaneously, since both modes may be passed simultaneously by filter 24 and both may be detected by oppositely biased detector electrodes 33, 35. Further advantageously, a bias on one electrode both attracts the oppositely charged ions and also deflects the same charged ions to the opposite detector electrode. Therefore a fast-operating DMS with high detection efficiency can be implemented in practices of the present invention. Prior art DMS/FAIMS devices have not benefited from such configuration.

The DMS spectral data listed in FIG. 9 suggest that explosives can be favorably separately and DMS-identified by their predictable and characteristic or signature interactions with specific dopants in practices of the invention. FIG. 10 shows electron affinities of listed explosives in relation to the electron affinities of the dopants. As seen in FIG. 10, the electron affinity of methylene bromide ($CH_2Br_2$) is lower than the electron affinity of the explosives HMX, Tetryl, PETN, RDX, and NG, but greater than the electron affinity of TNT and EGDN. Accordingly, each species is detected by its signature ionization. For example, electrons are transferred from methylene bromide to HMX, Tetryl, PETN, RDX, or NG, forming complexes that are detected through a signature shift of $V_C$. Conversely, TNT and EGDN are not detected with methylene bromide. Likewise, DNT can be detected with methanol and isopropanol, but not with $CH_2Br_2$ or $CH_2Cl_2$. A similar trend can be inferred for the positive ion species mode.

These results suggest that a miniaturized multi-channel DMS spectrometer can be envisioned, wherein each channel carries at least one of the dopants and receives an unknown mixture of analytes, such as the aforedescribed explosives. The values of the compensation voltages $V_C$ measured in each channel, in conjunction with the known electron/proton affinities, can then be used to reliably determine the chemical composition of the analyte. Those skilled in the art will appreciate that the use of dopants for the detection of explosives is merely exemplary, and that other chemicals can also be detected.

A new method of enhancing resolution or selectivity in differential mobility spectrometry has been developed through modification of the transport gas with a small amount of dopants and has been applied for the determination of explosives with the preferred DMS having a compact, platetype, "micro-fabricated" flow path (drift tube).

Addition of 1,000 ppm of methylene chloride into the purified air transport gas increased the field-dependence of the mobility for explosive ions 3-6 times, as expressed in the observed increase in the compensation voltage. As a result, it is clear that DMS practices of the invention enable detection of explosives substances on a part per billion level with a response time about approximately one second.

Also listed in the Table is DMNB which represents a taggant added to explosive materials for security purposes. DMNB has the chemical formula 2,3-dimethyl-2,3-dinitro-n-butane ($C_6H_{12}N_2O_4$). Taggants have experienced renewed interest due to government supported anti-terrorist activity, especially after Sep. 11, 2001. Use of taggants serves two different functions and thus uses two different kinds of taggants. A first type of taggant aids in the detection of explosives prior to detonation by using appropriate detection equipment. A second type of taggant is designed to survive an explosive blast and helps in the identification of the particular explosive material. It can be recovered at the bomb scene and provide traceable sourcing information related to the explosives' purchase history. The United States has officially designated DMNB as a detection taggant for plastic explosives.

Detection of taggants, like DMNB, is difficult with some analytical equipment, such as conventional ion mobility spectrometers (IMS), especially in real world environments such as airport security. DMS spectrometers of the invention, on the other hand, can be fine-tuned for specific chemical substances, as described above. As will be described below, DMS spectrometers can be used to detect taggants and to distinguish the taggant signal from that of the background. In addition to DMNB, o-MNT (ortho-mononitrotoluene) and p-MNT (para-mononitrotoluene) taggants, which are also listed in the Table, can also be detected.

We detect taggants, such as DNMB, in order to detect presence of an explosive in a sample. The following shows detection of 2,3-dimethyl-2,3-dinitro-n-butane ($C_6H_{12}N_2O_4$), commonly referred to as DMNB, as a detection taggant for plastic explosives. This is shown by way of illustration, not limitation.

Figure 11A:
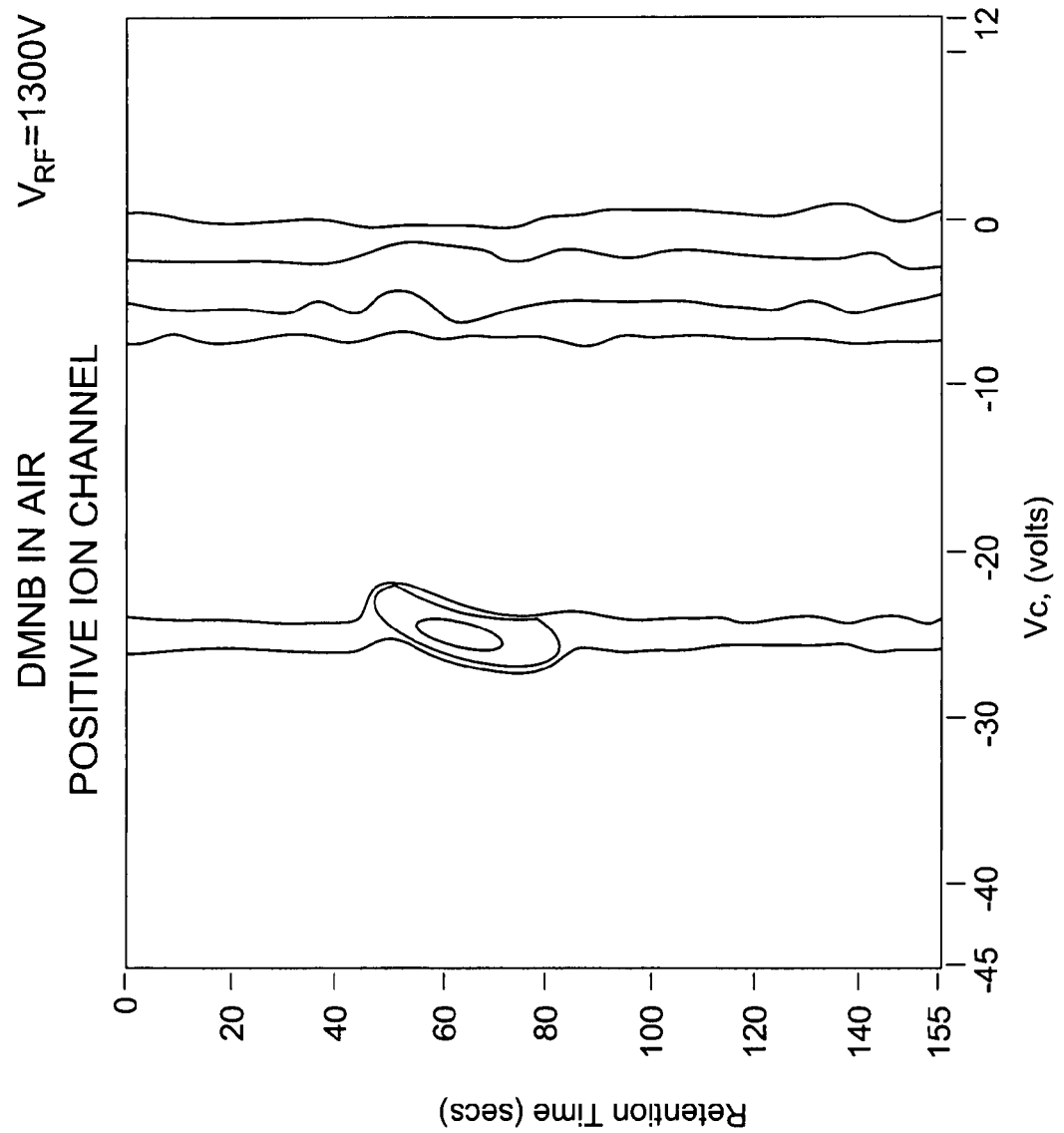
FIGS. 11A and 11B show DMS spectra for the positive and negative mode detections for a trace sample of DMNB in air at Vrf=1300V in practice of an embodiment of the invention.
Figure 11B:
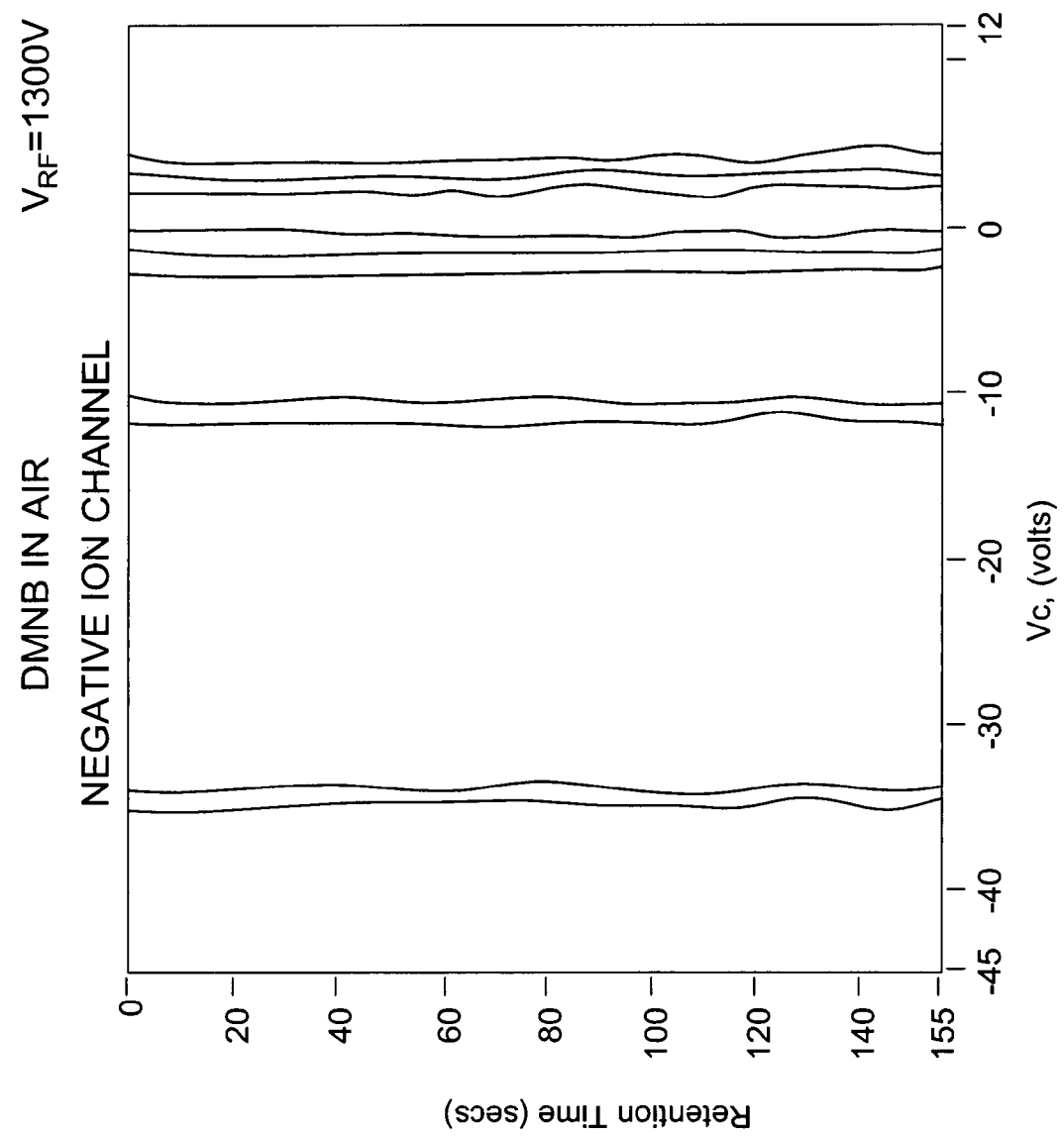

In one illustrative practice of the invention, FIG. 11 shows detection of DMNB taggant introduced at a trace amount of 200 micro liters in an air transport at 0.4 L/min is shown, with the DMS separation field operated at an RF having Rmax of 1300 v. DMNB fragment spectra are detected at about −25 Vc and a DMNB-related molecular spectra is at about −4 Vc. These positive mode detections (left frame) of DMNB taggant signature clearly stand out over the background spectra. Negative mode detections also show a small DMNB-related peak at around −31 Vc.

Figure 12A:
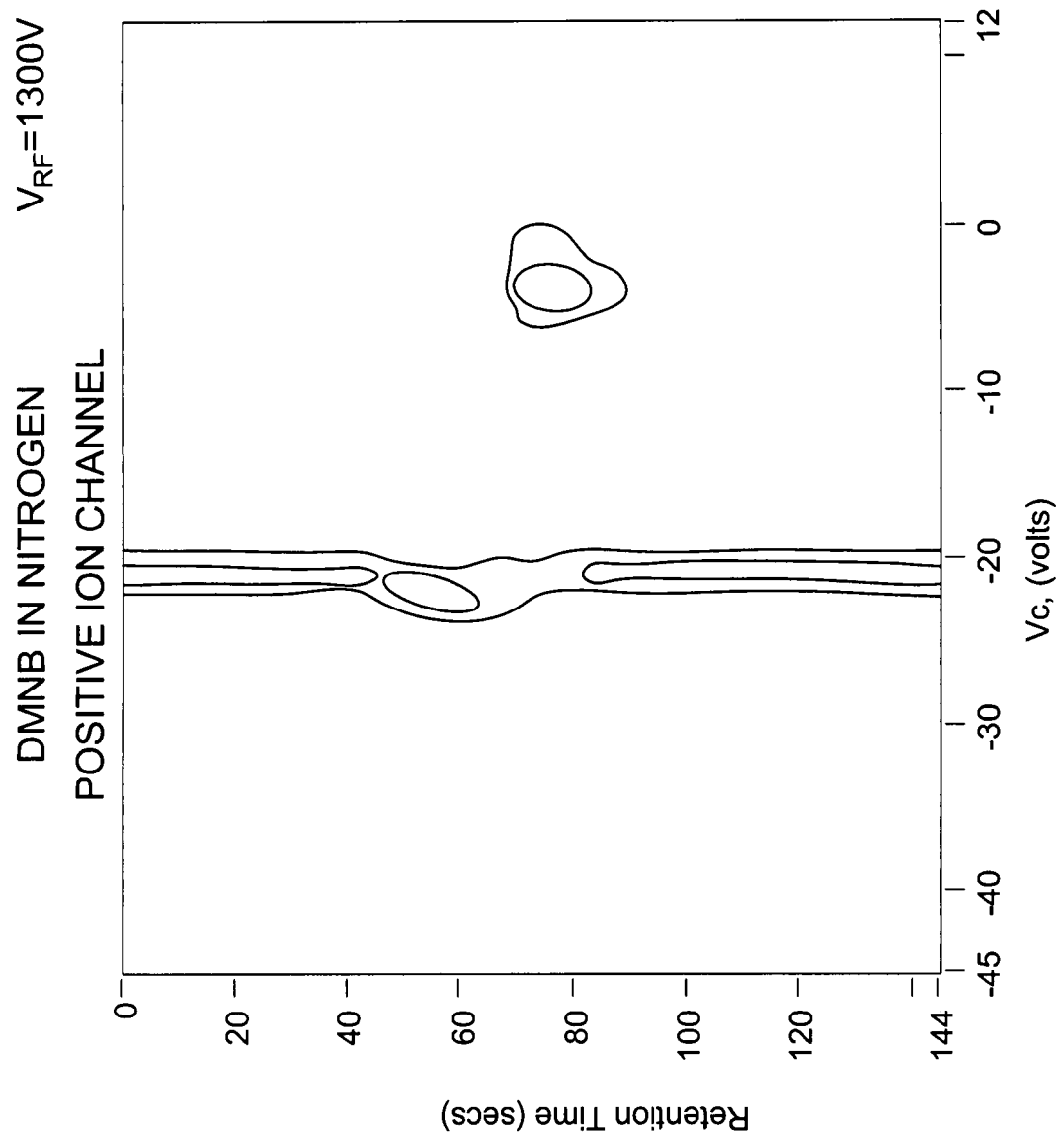
FIGS. 12A AND 12B show DMS spectra for positive and negative mode detections for a trace sample of DMNB in nitrogen at Vrf=1300V in practice of an embodiment of the invention.
Figure 12B:
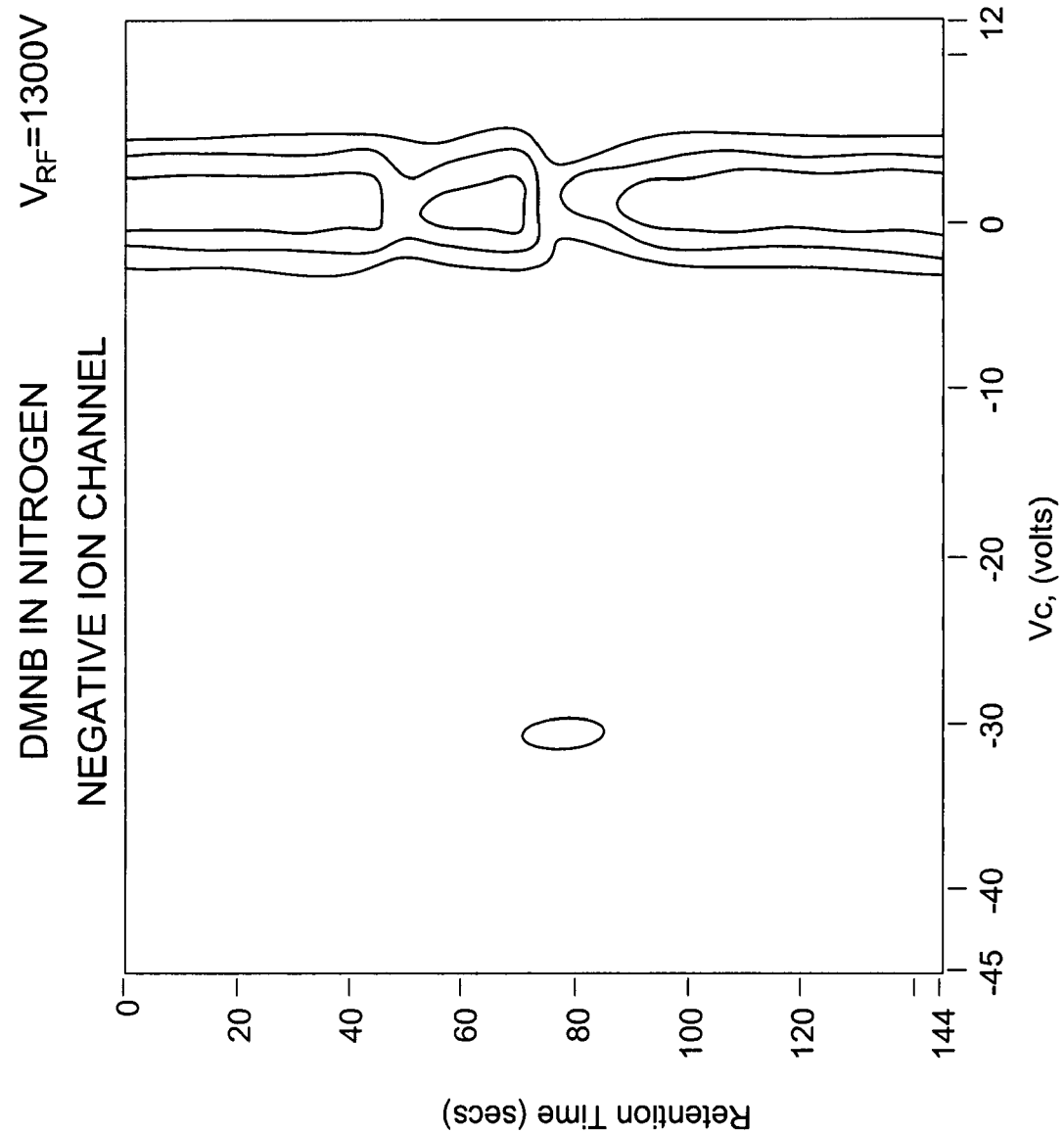

In FIG. 12 we show detection of DMNB taggant at 200 micro liters in a nitrogen gas transport at 0.4 L/min, with Rmax of 1300 v. DMNB fragment spectra are detected at about −21 Vc with a related molecular peak at about −4 Vc, in the positive mode (left frame). In addition, negative detection spectra are seen for a DMNB-related peak at about −31 Vc in the right frame. All are well separated from the background spectra.

Figure 13A:
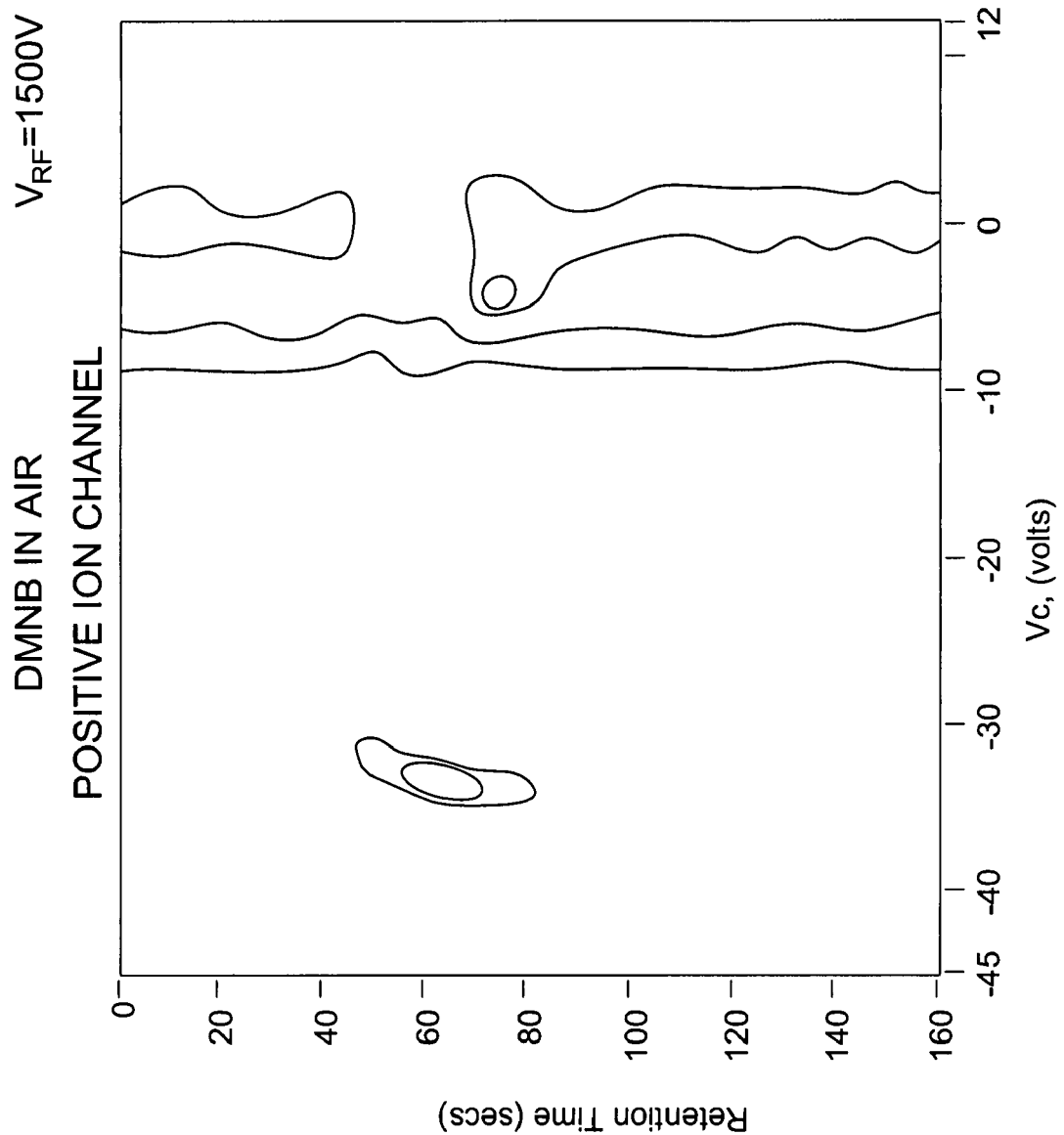
FIGS. 13A and 13B show DMS spectra for the positive and negative mode detections for a trace sample of DMNB in air at Vrf=1500V in practice of an embodiment of the invention.
Figure 13B:
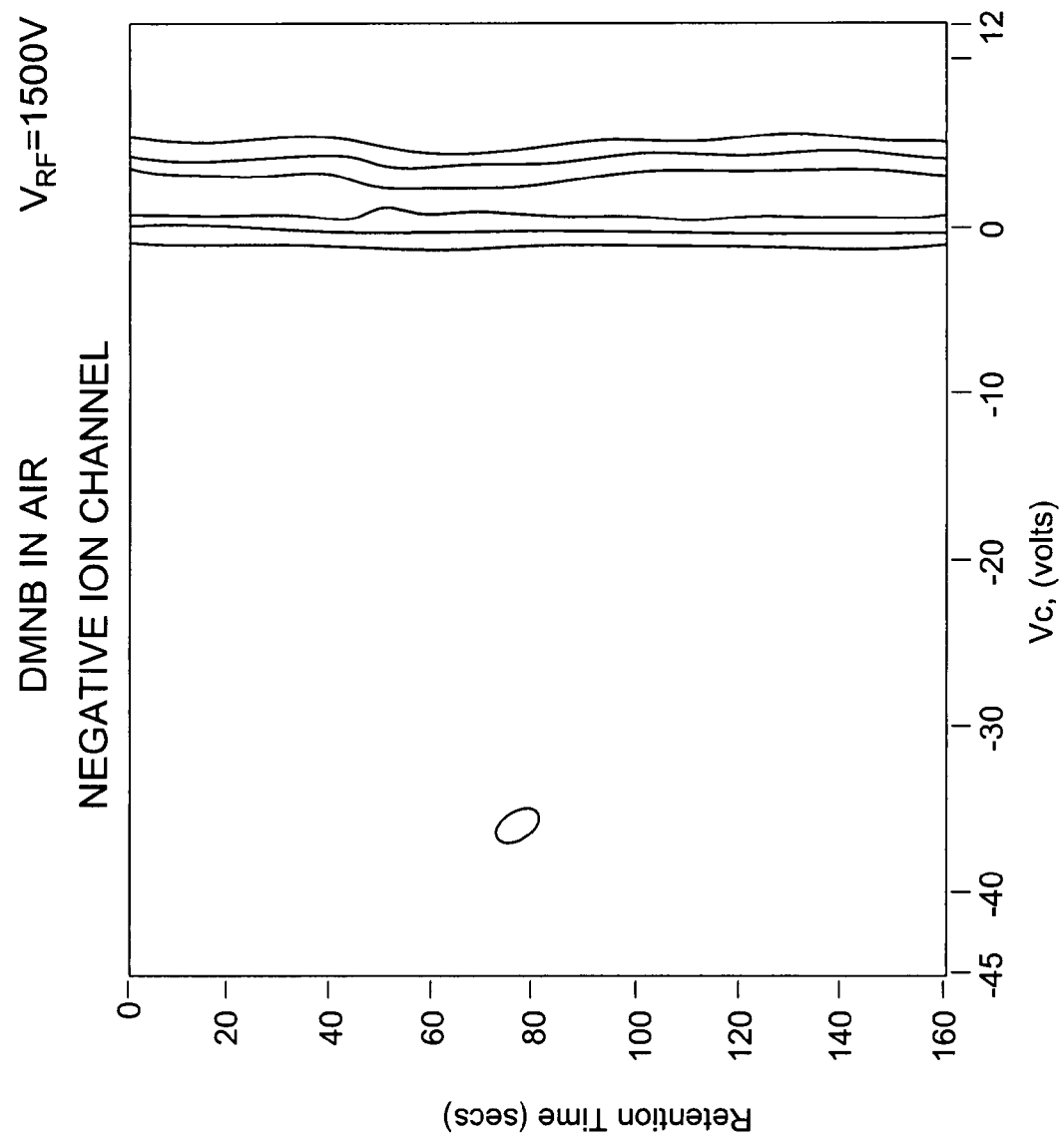

In FIG. 13, detection of DMNB taggant introduced at a trace amount of 200 micro liters in an air transport at 0.4 L/min is shown, with Rmax of 1500 v. Fragment spectra are detected at about −35 Vc and a molecular spectra is seen at about −4 Vc. These positive mode detections (left frame) of taggant signatures clearly stand out over the background spectra. As well a smaller DMNB signature peak is seen in the negative mode at about −35 Vc.

Figure 14A:
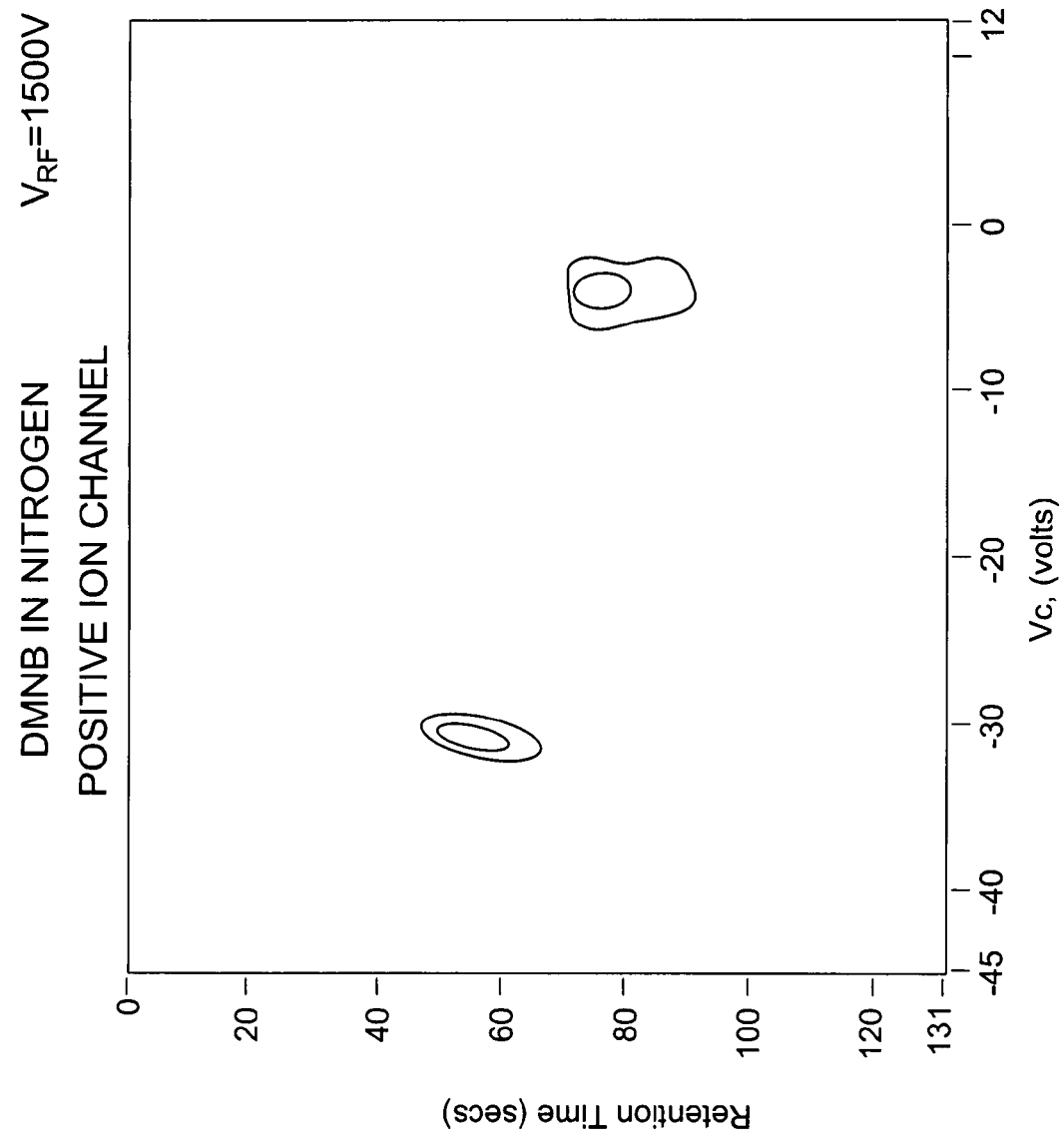
FIGS. 14A and 14B show DMS spectra for the positive and negative mode detections for a trace sample of DMNB in nitrogen at Vrf=1500V in practice of an embodiment of the invention.
Figure 14B:
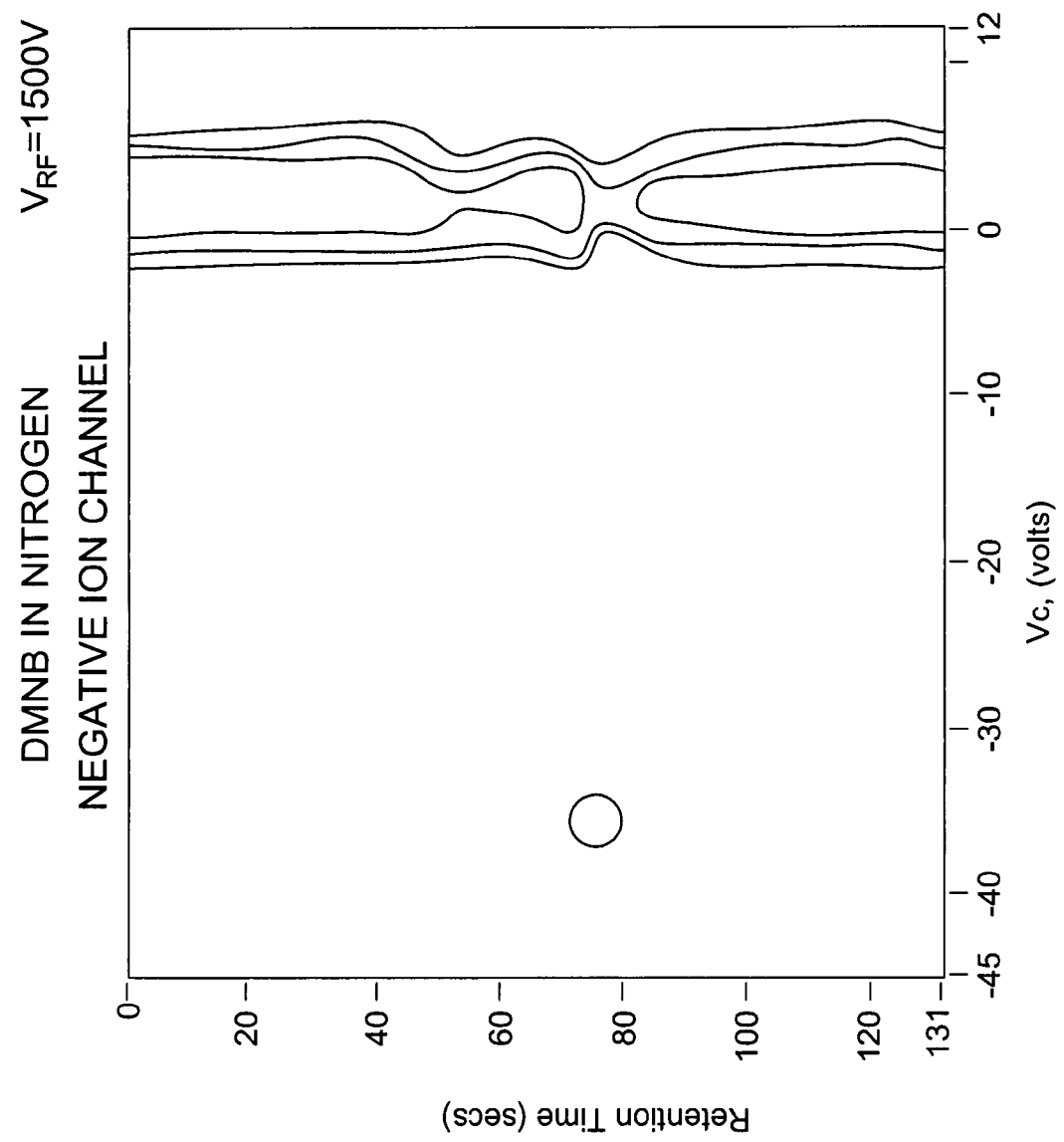

In FIG. 14 we show detection of taggant at 200 micro liters in a nitrogen gas transport at 0.4 L/min, with Rmax of 1500 v. Fragment spectra are detected at about −33 Vc with a molecular peak at about −4 Vc in the left frame. In addition, DNMB negative detection spectra are seen at about −38 Vc in the right frame. All are well separated from background spectra.

It will be appreciated that while it has been tried, resolving between taggants like DMNB and the background reactant ion peaks has been difficult or impossible using conventional IMS systems. Even prior art FAIMS systems have failed to demonstrate such capability. However, the present disclosure illustrates the ability of the DMS system of the invention to separate, detect and identify taggants. This can be achieved even in presence of complex backgrounds and including common explosives impurities such as toluene.

It should be appreciated that conventional IMS systems have experienced problems in resolving between taggants like DMNB and the background reactant ion peaks. Prior art DMS systems have also failed to demonstrate such capability. However, taggants have been successfully detected and identified in practice of embodiments of the invention. This can be achieved even in presence of complex backgrounds and including common explosives impurities such as toluene.

In a further aspect of the present invention, it will be appreciated that we detect known sample species, correlating RF field, compensation, pressure, humidity, and/or other parameters, such as dopant and gases used. We create a data store describing at least one analyte preferably at various parameter levels. In one embodiment, the data source is accessed as a lookup table and has a range of detections of explosives-related analytes.

In embodiments of the invention, we can detect and identify an explosives-related compound based on comparison to this stored data. A single comparison may be adequate where a system is dedicated to detection of a particular species. An optimized set of RF and compensation values may be selected, which may include values representing selected pressure. These optimized parameters are selected to meet the criterion of increased reliability in identification by detection data set. Presence or absence of a species can be indicated by conventional announcement means.

It will be further appreciated that it is possible to control operating conditions and to discriminate between compounds that are ordinarily difficult to separately identify by other means. Selection of operating conditions enables isolation of an ion species of interest. Furthermore, because the system of the invention matches detection data with stored data, we can select operating conditions that will produce detection data that is matchable to stored data, to determine a species is present in the sample.

It will now be appreciated by a person skilled in the art that we can optimize ion species analysis for explosives detection in practice of embodiments the invention by adjustment of field, DC compensation, frequency, duty cycle, asymmetry, pressure, flow rate, gas composition, moisture, and/or ionization type/energy, among other controls.

It will be further appreciated that in practice of the invention we optimize the DMS performance to enable improved explosives detection based on differences in ion mobility-related behavior. Species are separated, detected and identified based on this optimization. We can further optimize the process by detecting ion polarity, and we can optimize ionization and/or separation by using dopants. Thus in practice of the present invention, we apply various strategies for improved isolation, detection and identification of explosives-related chemicals in a sample based on aspects of differential ion mobility behavior.

It should, of course, also be appreciated that numerous changes may be made to the disclosed embodiments without departing from the scope of the present invention. While the foregoing examples refer to specific compounds, this is intended to be by way of example and illustration only, and not by way of limitation. It should be appreciated by a person skilled in the art that other molecules may be similarly ionized and detected, with or without the use of dopants, and/or pressure regulation, and/or humidity adjustment, and/or adjustment of the concentration of other polar molecules, in practice of the invention.

Therefore, while this invention has been particularly shown and described with reference to the above embodiments, it will be understood by those skilled in the art that various changes in form and details may be made therein without departing from the scope of the invention encompassed by the appended claims. Accordingly, the spirit and scope of the present invention is to be limited only by the following claims.

What is claimed is:

1. A system for analyzing a material including a taggant additive comprising:
    an ion mobility based filter for i) receiving material ions and taggant ions and ii) applying a time-varying field to the material ions and taggant ions, and
    a controller for adjusting at least one condition of the ion mobility based filter to separate a portion of the taggant ions from the material ions.

2. The system of claim 1, wherein the taggant includes a material capable of surviving an explosion.

3. The system of claim 2, wherein the taggant includes at least one of DMNB, o-MNT (ortho-mononitrotoluene) and p-MNT (para-mononitrotoluene).

4. The system of claim 3, wherein the material includes an explosive material.

5. The system of claim 4, wherein the explosive material includes at least one of HMX, Tetryl, PETN, RDX, NG, TNT, EGDN, DNT, o-MNT, p-MNT, DMNB, TATP, HMTD and AN.

6. The system of claim 1, wherein the condition includes one of an amount of a dopant, pressure level, magnitude of a compensation field, magnitude of the time-varying field, frequency of the time-varying field, duty cycle of the time-varying field, and flow rate.

7. The system of claim 1 comprising a gas chromatograph (GC) for introducing the material including a taggant to the ion mobility based filter.

8. The system of claim 1 comprising a detector for detecting at least one of the taggant ions and material ions that exit the ion mobility based filter.

9. The system of claim 8, wherein the detector includes a positively biased electrode and a negatively biased electrode.

10. The system of claim 1 comprising a data store including one or more sets of conditions of the filter associated with one or more spectra of the material ions and the taggant ions, wherein the controller is configured to compare a detected spectrum with the one or more spectra of the data store to identify one or both of the material and taggant additive.

11. A method for analyzing a material including a taggant additive comprising:
    flowing a portion of material ions and taggant ions through an ion mobility based filter,
    dispersing the material ions and taggant ions using a time-varying field, and
    adjusting at least one condition of the ion mobility based filter to separate a portion of the taggant ions from the material ions.

12. The method of claim 11, wherein the taggant includes a material capable of surviving an explosion.

13. The method of claim 11, wherein the taggant includes at least one of DMNB, o-MNT (ortho-mononitrotoluene) and p-MNT (para-mononitrotoluene).

14. The method of claim 11, wherein the material includes an explosive material.

15. The method of claim 14, wherein the explosive material includes at least one of HMX, Tetryl, PETN, RDX, NG, TNT, EGDN, DNT, o-MNT, p-MNT, DMNB, TATP, HMTD and AN.

16. The method of claim 11, wherein the condition includes one of an amount of a dopant, pressure level, magnitude of a compensation field, magnitude of the time-varying field, frequency of the time-varying field, duty cycle of the time-varying field, and flow rate.

17. The method of claim 11 comprising, prior to flowing a portion of material ions and taggant ions through the ion mobility based filter, eluting the material including the taggant from a gas chromatograph (GC).

18. The method of claim 11 comprising detecting at least one of the taggant ions and material ions that exit the ion mobility based filter.

19. The method of claim 18 comprising concurrently detecting positive and negative ions.

20. The method of claim 18 comprising comparing a detected spectrum with one or more spectra of a data store to identify one or both of the material and taggant additive at one or more sets of conditions of the filter associated with one or more spectra of the material ions and the taggant ions.

* * * * *